US010493285B2

(12) United States Patent
Yu et al.

(10) Patent No.: US 10,493,285 B2
(45) Date of Patent: Dec. 3, 2019

(54) METHODS AND SYSTEMS FOR MULTI-SITE STIMULATION

(71) Applicant: Cardiac Pacemakers, Inc., St. Paul, MN (US)

(72) Inventors: Yinghong Yu, Shoreview, MN (US); David J. Ternes, Roseville, MN (US); Keith L. Herrmann, Minneapolis, MN (US); Sunipa Saha, Shoreview, MN (US); Pratik K. Pandya, Minneapolis, MN (US); Jason Humphrey, New Brighton, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 50 days.

(21) Appl. No.: 15/603,720

(22) Filed: May 24, 2017

(65) Prior Publication Data

US 2017/0348528 A1    Dec. 7, 2017

Related U.S. Application Data

(60) Provisional application No. 62/344,238, filed on Jun. 1, 2016.

(51) Int. Cl.
| | | |
|---|---|---|
| *A61N 1/00* | (2006.01) | |
| *A61N 1/368* | (2006.01) | |
| *A61N 1/05* | (2006.01) | |
| *A61N 1/365* | (2006.01) | |
| *A61N 1/372* | (2006.01) | |
| *A61N 1/39* | (2006.01) | |

(52) U.S. Cl.
CPC ........... *A61N 1/3684* (2013.01); *A61N 1/056* (2013.01); *A61N 1/36521* (2013.01);
(Continued)

(58) Field of Classification Search
CPC .. A61N 1/056; A61N 1/36521; A61N 1/3684; A61N 1/36843; A61N 1/3686; A61N 1/37247; A61N 1/3956
See application file for complete search history.

(56) References Cited

U.S. PATENT DOCUMENTS

| | | |
|---|---|---|
| 7,620,452 B1 | 11/2009 | Russie |
| 8,055,343 B2 | 11/2011 | Gandhi et al. |

(Continued)

FOREIGN PATENT DOCUMENTS

| | | |
|---|---|---|
| CN | 109219468 A | 1/2019 |
| EP | 1937361 A1 | 7/2008 |

(Continued)

OTHER PUBLICATIONS

"International Application Serial No. PCT/US2017/034140, International Preliminary Report on Patentability dated Dec. 13, 2018", 7 pgs.

(Continued)

*Primary Examiner* — George Manuel
(74) *Attorney, Agent, or Firm* — Schwegman Lundberg & Woessner, P.A.

(57) ABSTRACT

Systems and methods for multi-site cardiac stimulation are disclosed. The system includes an electrostimulation circuit to deliver electrostimulation to one or more candidate sites of at least one heart chamber. The system may sense a physiological signal including during electrostimulation of the heart, use the physiological signal to determine a first stimulation vector for electrostimulation at a first left ventricular (LV) site and a second stimulation vector for electrostimulation at a different second LV site, and determine a therapy mode including a first chronological order and a first timing offset between stimulations delivered according to the first and second stimulation vectors. The electrostimulation circuit may deliver electrostimulation to the heart in (Continued)

accordance with the first and second stimulation vectors and the therapy mode.

20 Claims, 6 Drawing Sheets

(52) U.S. Cl.
 CPC ........ *A61N 1/37247* (2013.01); *A61N 1/3686* (2013.01); *A61N 1/36843* (2017.08); *A61N 1/3956* (2013.01)

(56) References Cited

U.S. PATENT DOCUMENTS

| | | | |
|---|---|---|---|
| 9,138,585 B2* | 9/2015 | Saha | ............ A61N 1/3686 |
| 2011/0098770 A1 | 4/2011 | Ryu et al. | |
| 2012/0035685 A1* | 2/2012 | Saha | ............ A61N 1/3686 607/59 |
| 2015/0165204 A1 | 6/2015 | Yu et al. | |
| 2015/0273218 A1 | 10/2015 | Rockweiler et al. | |

FOREIGN PATENT DOCUMENTS

| | | |
|---|---|---|
| WO | WO-2016061366 A1 | 4/2016 |
| WO | WO-2017210047 A1 | 12/2017 |

OTHER PUBLICATIONS

"International Application Serial No. PCT/US2017/034140, International Search Report dated Oct. 6, 2017", 4 pgs.

"International Application Serial No. PCT/US2017/034140, Written Opinion dated Oct. 6, 2017", 7 pgs.

* cited by examiner

METHODS AND SYSTEMS FOR MULTI-SITE STIMULATION

CLAIM OF PRIORITY

This application claims the benefit of priority under 35 U.S.C. §119(e) of U.S. Provisional Patent Application Ser. No. 62/344,238, filed on Jun. 1, 2016, which is herein incorporated by reference in its entirety.

TECHNICAL FIELD

This document relates generally to medical devices, and more particularly, to devices and methods for stimulating excitable tissue and evaluating resultant physiological response.

BACKGROUND

Congestive heart failure (CHF) is a leading cause of death in the United States. CHF occurs when the heart is unable to adequately supply enough blood to maintain a healthy physiological state. CHF may be treated by drug therapy, or by an implantable medical device (IMD) such as for providing cardiac pacing therapies, including resynchronization therapy (CRT) to correct cardiac dyssynchrony within a ventricle or between ventricles.

The IMD may chronically stimulate excitable tissues or organs, such as a heart, to treat abnormal cardiac rhythms or to help improve cardiac performance in a patient with CHF. Such ambulatory medical devices may have at least first and second electrodes that may be positioned within the heart or on a surface of the heart for contacting the cardiac tissue. The electrodes may be electrically coupled to an electronics unit such as a pulse generator, such as via a lead, and may be used to deliver one or more electrostimulations to the heart, such as to restore or to improve the normal heart function.

OVERVIEW

Cardiac stimulation using an implantable medical device (IMD) may involve one or more implantable leads that may be inserted into one of the heart chambers, such as an atrium or a ventricle. Stimulation of the heart may be accomplished through direct myocardium stimulation using at least first and second electrodes that may be electrically connected to the IMD and in close contact with the cardiac tissue. The electrodes may be positioned along the one or more implantable leads. The stimulation may be provided at specified stimulation strength (e.g., stimulation energy) sufficient to capture the heart tissue, that is, the stimulation may effectively cause depolarization propagating to a part or the entirety of the heart.

During the CRT therapy, synchronized stimulation may be applied to the left ventricle (LV) and the right ventricle (RV) of a heart. Conventionally, there may be one RV pacing site and one LV stimulation site. Stimulation of multiple sites on a chamber of the heart, such as pacing at multiple LV sites (which is known as multi-site LV stimulation), has been proposed as an alternative to the conventional single site CHF therapy. The multi-site stimulation may involve electrostimulation delivered at two or more sites in at least one heart chamber (such as LV) within a cardiac cycle, such as simultaneous stimulation or separated by a specified timing offset less than a sensed or paced time interval value of the cardiac cycle.

Although multi-site stimulation may have certain benefits, multi-site stimulation may require more energy than single site pacing, and may also increase the complexity of system design and operation. Identifying patients that are likely to benefit from multi-site stimulation and determining stimulation vectors may be clinically more challenging and technically more complex. Additionally, the efficacy of multi-site stimulation may be affected by the scheduling of pacing sequences at different sites, such as an order of delivering stimulations to different cardiac sites, timing offsets between the stimulations at different sites, or parameters associated with stimulation intensity, among others. The present inventors have recognized, among other things, that there remains a demand for systems and methods to effectively and efficiently program the multi-site cardiac stimulation, so as to improve the patient outcome.

This document discusses, among other things, a system for programming an electrostimulator to deliver multi-site cardiac stimulation. The system may include an electrostimulation circuit to deliver electrostimulation to one or more candidate sites of at least one heart chamber. The system may sense a physiological signal including during electrostimulation of the heart, use the physiological signal to determine at least a first stimulation vector for electrostimulation at a first left ventricular (LV) site and a second stimulation vector for electrostimulation at a different second LV site. The system may determine a therapy mode including a first chronological order and a first timing offset between stimulations delivered according to the first and second LV stimulation vectors. The electrostimulation circuit may deliver multi-site electrostimulation of the heart in accordance with the first and second stimulation vectors and the therapy mode.

Example 1 is a system that comprises an electrostimulation circuit configured to deliver electrostimulation to one or more sites in at least one chamber of a heart, a sensor circuit including a sense amplifier to sense a physiological signal including during the electrostimulation of the one or more candidate sites, and a therapy programmer circuit in communication with the sensor circuit. The therapy programmer circuit may be configured to determine, using the sensed physiological signal, a first stimulation vector for electrostimulation at a first left ventricular (LV) site, and to determine, based on the first stimulation vector, a second stimulation vector for electrostimulation at a different second LV site. The first stimulation vector includes a first LV cathode and a first anode, and the second stimulation vector includes a second LV cathode and a second anode. The therapy programmer circuit may also determine a therapy mode including one or more of a first chronological order or a first timing offset between (1) a first LV stimulation delivered according to the first stimulation vector and (2) a second LV stimulation delivered according to the second stimulation vector. The system comprises a controller circuit to configure the electrostimulation circuit to deliver the first and second LV stimulations according to the therapy mode.

In Example 2, the subject matter of Example 1 optionally includes the sensor circuit that may be configured to detect, from the sensed physiological signal, activations at the first and second LV sites, and to determine a first activation delay from the activation at the first LV site with respect to a reference time, and a second activation delay from the activation at the second LV site with respect to the reference time. The therapy programmer circuit may determine the first chronological order or the first timing offset based on the first and second activation delays.

In Example 3, the subject matter of Example 2 optionally includes the reference time which may include a RV activation within the same cardiac cycle as the activations at the first and second LV sites. The therapy programmer circuit may determine the one or more of the first chronological order or the first timing offset including: the first LV stimulation substantially simultaneously delivered with the second LV stimulation, when the first activation delay is substantially no greater than the second activation delay; or the first LV stimulation preceding the second LV stimulation by the first timing offset proportional to a difference between the first activation delay and the second activation delay, when the first activation delay is substantially greater than the second activation delay.

In Example 4, the subject matter of any one or more of Examples 1-3 optionally includes the therapy programmer circuit that may further be configured to determine a third stimulation vector for electrostimulation at a third cardiac site different from the first and second LV sites. The therapy mode may include one or more of a second chronological order or a second timing offset between (1) a third cardiac stimulation delivered according to the third stimulation vector and (2) the first or second LV stimulation.

In Example 5, the subject matter of Example 4 optionally includes the third cardiac site that may include a right ventricular (RV) site. The third stimulation vector may include a RV cathode and an anode including one of: a can electrode; a RV electrode different than the RV cathode; a right atrium electrode; or a superior vena cava electrode.

In Example 6, the subject matter of Example 5 optionally includes the sensor circuit that may be configured to detect from the sensed physiological signal a LV activation and a RV activation within the same cardiac cycle, and to determine a RV-LV delay from the detected LV activation to the detected RV activation. The therapy programmer circuit may determine the second chronological order or the second timing offset based at least on the RV–LV delay, which may include the first and second LV stimulations preceding the third cardiac stimulation by a programmable offset when the RV–LV delay exceeds a specified threshold, and the third cardiac stimulation preceding the first and second LV stimulations by a programmable offset when the RV–LV delay falls below the specified threshold.

In Example 7, the subject matter of any one or more of Examples 1-6 optionally includes the electrostimulation circuit that may be configured to deliver electrostimulation according to each of a plurality of candidate LV stimulation vectors. Each candidate LV stimulation vector includes a LV cathode and an anode selected from the group consisting of a can electrode, a RV electrode, a right atrium electrode, a superior vena cava electrode and a different LV electrode. The sensor circuit may be configured to generate, from the physiological signal sensed during the electrostimulation, one or more response characteristics associated with respective candidate LV stimulation vector; and the therapy programmer circuit is configured to determine the first stimulation vector including identify from the plurality of candidate LV stimulation vectors a LV stimulation vector with the corresponding one or more response characteristics satisfying a specified condition.

In Example 8, the subject matter of Example 7 optionally includes the one or more response characteristics that may include an indication of phrenic nerve stimulation (PNS), an impedance measurement; a RV to LV activation delay (VVD), or a LV stimulation threshold.

In Example 9, the subject matter of Example 8 optionally includes the therapy programmer circuit that may be configured to select from the plurality of candidate LV stimulation vectors the first stimulation vector including: identify a first set of candidate LV stimulation vectors with substantially no PNS indication and the corresponding impedance measurements falling within a specified range; select from the first set of candidate LV stimulation vectors a second set of candidate LV stimulation vectors each having substantially longer VVD than other of the first set of candidate LV stimulation vectors. If the second set of candidate LV stimulation vectors incudes only one vector, then the only one vector is determined to be the first stimulation vector. If the second set of candidate LV stimulation vectors includes more than one vector, then the first stimulation vector is selected from the second set as a vector having a substantially smaller LV stimulation threshold than other of the second set of candidate LV stimulation vectors.

In Example 10, the subject matter of any one or more of Examples 8-9 optionally includes the therapy programmer circuit that may be configured to determine the second stimulation vector, including: identify the second LV cathode selected from cathodes of the plurality of candidate LV stimulation vectors, the second LV cathode spatially more distant from the first cathode than other of the cathodes of the plurality of candidate LV stimulation vectors; and select, from a third set of candidate LV stimulation vectors each having the second LV cathode, the second stimulation vector associated with a substantially smaller LV stimulation threshold than other of the third set of candidate LV stimulation vectors.

In Example 11, the subject matter of Example 1 optionally includes the therapy programmer circuit that may be configured to determine the second stimulation vector using information about electrodes on a lead.

In Example 12, the subject matter of Example 11 optionally includes the therapy programmer circuit that may be configured to determine the second stimulation vector using a relative inter-electrode distance.

In Example 13, the subject matter of Example 12 optionally includes a lead including a distal LV electrode and two or more proximal LV electrodes. The distal LV electrode has an inter-electrode distance substantially greater than inter-electrode distance among the two or more proximal LV electrodes. If the first LV cathode is determined as one of the proximal LV electrodes, then the therapy programmer circuit may be configured to determine the second LV cathode as the distal electrode, and select from a set of candidate LV stimulation vectors each having a cathode being the distal LV electrode the second stimulation vector that has a substantially smaller LV stimulation threshold than other of the set of candidate LV stimulation vectors. If the first LV cathode is determined to be the distal LV electrode, then the therapy programmer circuit may be configured to select, from a set of candidate LV stimulation vectors each having a cathode being one of the proximal LV electrodes, the second stimulation vector that has a substantially smaller LV stimulation threshold than other of the set of candidate LV stimulation vectors.

In Example 14, the subject matter of Example 12 optionally includes a lead including a plurality of LV distal electrodes and a plurality of LV proximal electrodes, the distal and proximal LV electrodes substantially equally spaced on the lead. If the first LV cathode is determined as one of the proximal LV electrodes, then the therapy programmer circuit may be configured to select, from a first set of candidate LV stimulation vectors each having a cathode being one of the distal LV electrodes, the second stimulation vector that has a substantially smaller LV stimulation threshold than other of the first set of candidate LV stimulation vectors. If the first LV cathode is determined as one of the distal LV electrodes, then the therapy programmer circuit may be configured to select, from a second set of candidate LV stimulation vectors each having a cathode being one of the proximal LV electrodes, the second stimulation vector that has a substantially smaller LV stimulation threshold than other of the second set of candidate LV stimulation vectors.

In Example 15, the subject matter of any one or more of Examples 1-14 optionally includes the therapy programmer circuit that may be configured to determine the therapy mode including determine one or more stimulation parameters for the first and second LV stimulation based on one or more of LV stimulation threshold at the first and second LV sites or complication indicators.

Example 16 is a system that comprises an ambulatory medical device. The ambulatory medical device may include an electrostimulation circuit configured to deliver electrostimulation to one or more sites in at least one chamber of a heart, a sensor circuit including a sense amplifier to sense a physiological signal including during the electrostimulation of the one or more candidate sites, and a programmer device in communication with the ambulatory medical device. The programmer device may include a therapy programmer circuit in communication with the sensor circuit, and configured to: determine, using the sensed physiological signal, a first stimulation vector for electrostimulation at a first left ventricular (LV) site, the first stimulation vector including a first LV cathode and a first anode; determine, based on the first stimulation vector, a second stimulation vector for electrostimulation at a different second LV site, the second stimulation vector including a second LV cathode and a second anode; and determine a therapy mode including one or more of a first chronological order or a first timing offset between (1) a first LV stimulation delivered according to the first stimulation vector and (2) a second LV stimulation delivered according to the second stimulation vector. The programmer device may include a user input unit coupled to the therapy programmer circuit, and configured to receive user instructions including the first and second LV stimulation vectors and the therapy mode.

Example 17 is a method for automatically programming multi-site electrostimulation via an electrostimulation system. The method comprises steps of: delivering electrostimulation to one or more sites in at least one chamber of a heart according to a plurality of candidate electrostimulation vectors; sensing a physiologic signal including during the delivery of the electrostimulation; determining, using the sensed physiological signal, a first stimulation vector for electrostimulation at a first left ventricular (LV) site, the first stimulation vector including a first LV cathode and a first anode; determining, based on the first stimulation vector, a second stimulation vector for electrostimulation at a different second LV site, the second stimulation vector including a second LV cathode and a second anode; and determining a therapy mode for multi-site electrostimulation of at least the first and second LV sites, the therapy mode including one or more of a first chronological order or a first timing offset between (1) a first LV stimulation delivered according to the first stimulation vector and (2) a second LV stimulation delivered according to the second stimulation vector.

In Example 18, the subject matter of Example 17 optionally includes sensing from the sensed physiological signal activations at the first and second LV sites, and detecting a first activation delay from the activation at the first LV site with respect to a reference time, and a second activation delay from the activation at the second LV site with respect to the reference time. The first chronological order or the first timing offset is determined based on the first and second activation delays.

In Example 19, the subject matter of any one or more of Examples 17-18 optionally includes steps of: determining a third stimulation vector for electrostimulation at a third cardiac site at a right ventricle (RV), the third stimulation vector including a RV cathode and an anode; detecting from the sensed physiological signal a LV activation and a RV activation within the same cardiac cycle; and determining a RV–LV delay from the detected LV activation to the detected RV activation. The therapy mode determination may further include determining one or more of a second chronological order or a second timing offset between (1) a third cardiac stimulation delivered according to the third stimulation vector and (2) the first or second LV stimulation based at least on the RV–LV delay.

In Example 20, the subject matter of any one or more of Examples 17-19 optionally includes the determination of the first stimulation vector that may include steps of: delivering electrostimulation according to each of a plurality of candidate LV stimulation vectors; generating, from the physiological signal sensed during the electrostimulation, one or more response characteristics associated with respective candidate LV stimulation vector; and identifying from the plurality of candidate LV stimulation vectors a LV stimulation vector with the corresponding one or more response characteristics satisfying a specified condition. Each candidate LV stimulation vector may include a LV cathode and an anode selected from the group consisting of a can electrode, a RV electrode, a right atrium electrode, a superior vena cava electrode and a different LV electrode. The response characteristics may include an indication of phrenic nerve stimulation (PNS), an impedance measurement, a RV to LV activation delay (VVD), or a LV stimulation threshold.

In Example 21, the subject matter of any one or more of Examples 17-20 optionally includes the determination of the second stimulation vector, which may include steps of: identifying, from cathodes of the plurality of candidate LV stimulation vectors, the second LV cathode that is spatially more distant from the first cathode than other of the cathodes of the plurality of candidate LV stimulation vectors; and selecting, from a third set of candidate LV stimulation vectors each having the second LV cathode, the second stimulation vector associated with a substantially smaller LV stimulation threshold than other of the third set of candidate LV stimulation vectors.

In Example 22, the subject matter of any one or more of Examples 17-21 optionally includes the second stimulation vector that may be determined further using information about relative inter-electrode distance among electrodes on a lead.

In Example 23, the subject matter of any one or more of Examples 17-22 optionally includes the determination of the therapy mode that may further include determining one or more stimulation parameters for the first and second LV stimulation based on one or more of LV stimulation threshold at the first and second LV sites or complication indicators.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for programming multi-site stimulation for stimulating a heart. The multi-site stimulation may be delivered at various sites of the left ventricle (LV) of the heart to restore or improve cardiac performance. According the disclosed systems and methods, the physiological signals sensed at multiple cardiac sites during electrostimulation or during an intrinsic heart rhythm may be analyzed to determine at least two LV stimulation vectors. A therapy mode, which may include chronological order and timing offset between the stimulations according to the at least two stimulation vectors may be determined and used in a multi-site stimulation therapy.

Figure 1:
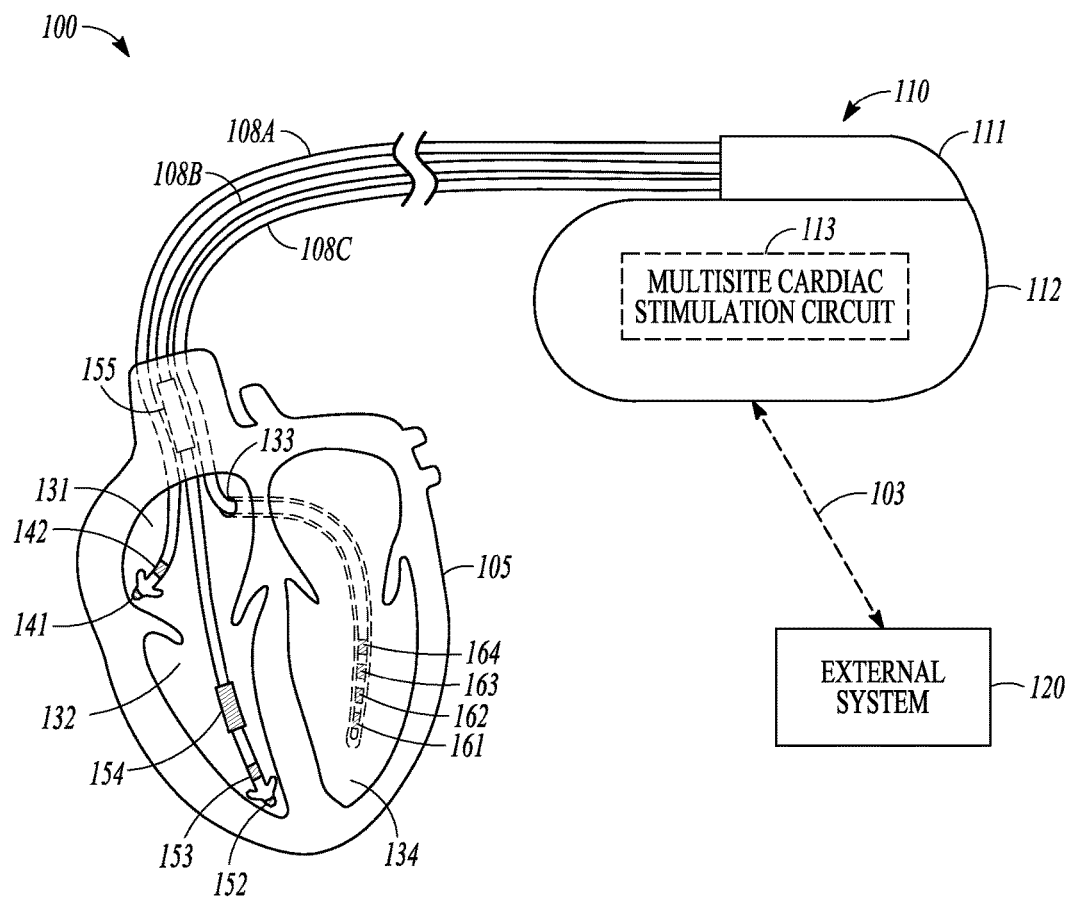
FIG. 1 illustrates generally an example of a Cardiac Rhythm Management (CRM) system and portions of an environment in which the CRM system may operate.

FIG. 1 illustrates generally an example of a Cardiac Rhythm Management (CRM) system 100 and portions of an environment in which the CRM system 100 may operate. The CRM system 100 may include an ambulatory medical device, such as an implantable medical device (IMD) 110 that may be electrically coupled to a heart 105 such as through one or more leads 108A-C, and an external system 120 that may communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 may include one or more monitoring or therapeutic devices such as a subcutaneously implanted device, a wearable external device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor.

As illustrated in FIG. 1, the IMD 110 may include a hermetically sealed may 112 that may house an electronic circuit that may sense a physiological signal in the heart 105 and may deliver one or more therapeutic electrical pulses to a target region, such as in the heart, such as through one or more leads 108A-C. The CRM system 100 may include only one lead such as 108B, or may include two leads such as 108A and 108B.

The lead 108A may include a proximal end that may be configured to be connected to IMD 110 and a distal end that may be configured to be placed at a target location such as in the right atrium (RA) 131 of the heart 105. The lead 108A may have a first pacing-sensing electrode 141 that may be located at or near its distal end, and a second pacing-sensing electrode 142 that may be located at or near the electrode 141. The electrodes 141 and 142 may be electrically connected to the IMD 110 such as via separate conductors in the lead 108A, such as to allow for sensing of the right atrial activity and optional delivery of atrial pacing pulses. The lead 108B may be a defibrillation lead that may include a proximal end that may be connected to IMD 110 and a distal end that may be placed at a target location such as in the right ventricle (RV) 132 of heart 105. The lead 108B may have a first pacing-sensing electrode 152 that may be located at distal end, a second pacing-sensing electrode 153 that may be located near the electrode 152, a first defibrillation coil electrode 154 that may be located near the electrode 153, and a second defibrillation coil electrode 155 that may be located at a distance from the distal end such as for superior vena cava (SVC) placement. The electrodes 152 through 155 may be electrically connected to the IMD 110 such as via separate conductors in the lead 108B. The electrodes 152 and 153 may allow for sensing of a ventricular electrogram and may optionally allow delivery of one or more ventricular pacing pulses, and electrodes 154 and 155 may allow for delivery of one or more ventricular cardioversion/defibrillation pulses. In an example, the lead 108B may include only three electrodes 152, 154 and 155. The electrodes 152 and 154 may be used for sensing or delivery of one or more ventricular pacing pulses, and the electrodes 154 and 155 may be used for delivery of one or more ventricular cardioversion or defibrillation pulses. The lead 108C may include a proximal end that may be connected to the IMD 110 and a distal end that may be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C may include an electrode 161 that may be located at a distal end of the lead 108C and another electrode 162 that may be located near the electrode 161. The electrodes 161 and 162 may be electrically connected to the IMD 110 such as via separate conductors in the lead 108C such as to allow for sensing the LV electrogram and optionally allow delivery of one or more resynchronization pacing pulses from the LV. Additional electrodes may be included in or along the lead 108C. In an example, as illustrated in FIG. 1, a third electrode 163 and a fourth electrode 164 may be included in the lead 108. In some examples (not shown in FIG. 1), at least one of the leads 108A-C, or an additional lead other than the leads 108A-C, may be implanted under the skin surface without being within at least one heart chamber, or at or close to heart tissue.

The IMD 110 may include an electronic circuit that may sense a physiological signal. The physiological signal may include an electrogram or a signal representing mechanical function of the heart 105. The hermetically sealed may 112 may function as an electrode such as for sensing or pulse delivery. For example, an electrode from one or more of the leads 108A-C may be used together with the can housing 112 such as for unipolar sensing of an electrogram or for delivering one or more pacing pulses. A defibrillation electrode from the lead 108B may be used together with the can housing 112 such as for delivering one or more cardioversion/defibrillation pulses. In an example, the IMD 110 may sense impedance such as between electrodes located on one or more of the leads 108A-C or the can housing 112. The IMD 110 may be configured to inject current between a pair of electrodes, sense the resultant voltage between the same or different pair of electrodes, and determine impedance using Ohm's Law. The impedance may be sensed in a bipolar configuration in which the same pair of electrodes may be used for injecting current and sensing voltage, a tripolar configuration in which the pair of electrodes for current injection and the pair of electrodes for voltage sensing may share a common electrode, or tetrapolar configuration in which the electrodes used for current injection may be distinct from the electrodes used for voltage sensing. In an example, the IMD 110 may be configured to inject current between an electrode on the RV lead 108B and the can housing 112, and to sense the resultant voltage between the same electrodes or between a different electrode on the RV lead 108B and the can housing 112. A physiological signal may be sensed from one or more physiological sensors that may be integrated within the IMD 110. The IMD 110 may also be configured to sense a physiological signal from one or more external physiological sensors or one or more external electrodes that may be coupled to the IMD 110. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiological response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 may include a multi-site cardiac stimulation circuit 113. The multi-site cardiac stimulation circuit 113 may be configured to detect physiological responses to electrostimulation at one or more candidate sites of the heart 105, such as electrostimulation of the left ventricle (LV) 134 via one or more of the electrodes 161-164 on the lead 108C. The physiological responses may include cardiac electrical signals or cardiac mechanical signals. The multi-site cardiac stimulation circuit 113 may use the physiological signal to determine at least a first stimulation vector for electrostimulation at a first LV site and a second stimulation vector for electrostimulation at a different second LV site, and determine a therapy mode including a first chronological order and a first timing offset between a first LV stimulation delivered according to the first stimulation vector and a second LV stimulation delivered according to the second stimulation vector. The electrostimulation circuit may deliver electrostimulation to the heart in accordance with the first and second stimulation vectors and the therapy mode. Examples of the multi-site cardiac stimulation circuit 113 are described below, such as with reference to FIGS. 2-4.

The external system 120 may allow for programming of the IMD 110 and may receive information about one or more signals acquired by IMD 110, such as may be received via a communication link 103. The external system 120 may include a local external IMD programmer. The external system 120 may include a remote patient management system that may monitor patient status or adjust one or more therapies such as from a remote location.

The communication link 103 may include one or more of an inductive telemetry link, a radio-frequency telemetry link, or a telecommunication link, such as an internet connection. The communication link 103 may provide for data transmission between the IMD 110 and the external system 120. The transmitted data may include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that may include physiological data acquisition such as using programmably specifiable sensing electrodes and configuration, device self-diagnostic test, or delivery of one or more therapies.

The multi-site cardiac stimulation circuit 113 may be implemented at the external system 120 such as using data extracted from the IMD 110 or data stored in a memory within the external system 120. Portions of the multi-site cardiac stimulation circuit 113 may be distributed between the IMD 110 and the external system 120.

Portions of the IMD 110 or the external system 120 may be implemented using hardware, software, or any combination of hardware and software. Portions of the IMD 110 or the external system 120 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
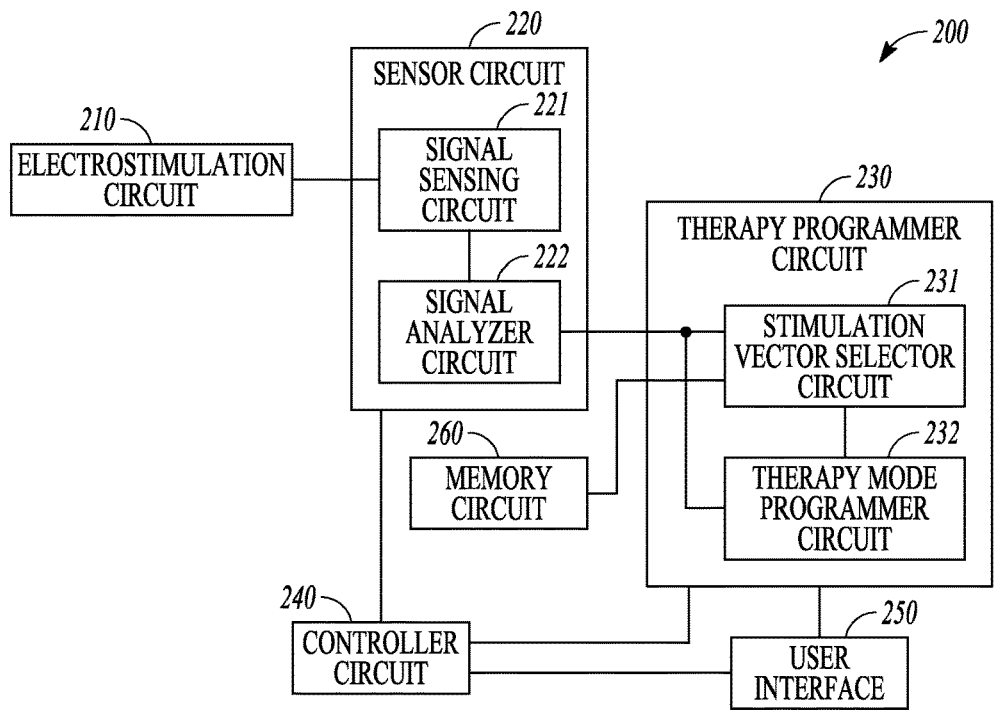
FIG. 2 illustrates generally an example of a multi-site electrostimulation circuit.

FIG. 2 illustrates generally an example of a multi-site electrostimulation circuit 200, which may be an embodiment of the multi-site cardiac stimulation circuit 113. The multi-site electrostimulation circuit 200 may include one or more of an electrostimulation circuit 210, a sensor circuit 220, a therapy programmer circuit 230, a controller circuit 240, a user interface 250, and a memory circuit 260.

The electrostimulation circuit 210 may be configured to deliver electrostimulation to a heart, such as one or more candidate sites of at least one chamber of the heart. The electrostimulation, such as a pulse train, may be produced by the IMD 100 or an external pulse generator, and delivered to the one or more candidate sites of the heart via a pacing delivery system such as one or more of the leads 108A-C and the respectively attached electrodes. The electrostimulation may be delivered between an anode and a cathode. The anode and the cathode form a stimulation vector. The electrostimulation may include a unipolar or a bipolar pacing configuration. The unipolar pacing may involve stimulation between an electrode positioned at or near a target stimulation site of the heart (such as an electrode on one of the leads 108A-C), and a return electrode such as the IMD can housing 112. The bipolar pacing may involve stimulation between two electrodes on one or more of the leads 108A-C.

The electrostimulation circuit 210 may be configured to deliver uni-site stimulation for stimulating one cardiac site, or multi-site stimulation for stimulating two or more sites of the heart within the same cardiac cycle. During multi-site stimulation, pulse trains may be delivered respectively at the two or more cardiac sites in accordance with a therapy mode. The therapy mode may include simultaneous stimulations, or sequential stimulations separated by a timing offset. The timing offset may be programmable and less than a sensed or paced time interval value of the cardiac cycle. As to be discussed in the following, the therapy mode may be determined by the therapy programmer circuit 230.

The multi-site stimulation may be delivered at two or more sites inside, or on an epicardial surface of, one or more heart chambers, including right atrium (RA), right ventricle (RV), left atrium (LA), and left ventricle (LV), or tissues surrounding any of the chambers. In an example, the multi-site stimulation may include stimulations at two or more sites of the same chamber, such as two or more sites in LV which is hereinafter referred to as "multi-site LV stimulation." The multi-site LV stimulation may be achieved using two or more LV stimulation vectors. Each LV stimulation vector includes an anode and a cathode. In an example, the LV stimulation vector can have a unipolar configuration where only one electrode (such as the cathode) is a LV electrode and the other electrode (such as the anode) is the IMD can housing 112. In an example, the LV stimulation vector can have a true bipolar configuration where both the cathode and anode are LV electrodes. In another example, the LV stimulation vector can have an extended bipolar configuration where one electrode (such as the cathode) is a LV electrode and the other electrode (such as the anode) is a RA electrode such as one of the electrodes 141 or 142, or a RV electrode such as one of the electrodes 152-155. In yet another example, the LV stimulation vector can have a tripolar configuration that involves, for example, two LV electrodes used jointly as the cathode, or two electrodes such as selected from the RA and RV electrodes used jointly as the anode. In some examples, one or more LV electrodes may be distributed in one or more LV leads, catheters, or untethered pacing units. The electrostimulation may be delivered to the two or more sites within a cardiac cycle, such as simultaneous stimulation or asynchronous stimulation separated by a specified timing offset less than a sensed or paced time interval value of the cardiac cycle.

The sensor circuit 220 may include a signal sensing circuit 221 and a signal analyzer circuit 222. The signal sensing circuit 221 may include a sense amplifier to sense a physiological signal. The signal sensing may be performed when the heart undergoes an intrinsic rhythm such as a sinus rhythm, or when the heart undergoes stimulation in accordance with a specified stimulation protocol. The physiological signal may include cardiac electrical signals such as electrocardiograms (ECGs) such as sensed by using electrodes non-invasively attached to the body surface, subcutaneous ECGs such as sensed by using subcutaneously placed electrodes, or intracardiac electrograms (EGMs) such as sensed by using electrodes on one or more of the leads 108A-C or the can housing 112. Additionally or alternatively, the physiological signals may also include signals indicative of cardiac mechanical activities such as contractions of an atrium or a ventricle as a response to an intrinsic heart rhythm or a stimulation of the heart. In an example, the cardiac mechanical activities may include a signal sensed from an ambulatory accelerometer or a microphone configured to sense the heart sounds in a patient. In an example, the cardiac mechanical activities may include a signal sensed from an impedance sensor configured to sense cardiac or thoracic impedance change as a result of cyclic cardiac contractions. The cardiac mechanical signals may include pressure sensor signals or any other sensor signals indicative of cardiac contractions.

In some examples, the signal sensing circuit 221 may simultaneously or sequentially sense two or more physiological signals such as from different sites on or within a heart chamber such as a left ventricle (LV). The signal sensing circuit 221 may sense two or more physiological signals from two or more LV sites using respective sensing vectors each including at least one of electrodes 161-164 on the LV lead 108C. An example of the LV sensing vector may include a bipolar sensing vector such as between a pair of electrodes selected among 161-164, or between one of the electrodes 161-164 and another electrode positioned on a different chamber or on a different lead (such as one of electrodes 152-155 on the RV lead 108B, or electrodes 141 or 142 on the RA lead 108A). Another example of the LV sensing vector may include a unipolar sensing vector such as between one of the electrodes 161-164 and the can housing 112.

The signal analyzer circuit 222 may process the sensed physiological signal including amplification, digitization, filtering, or other signal conditioning operations. The signal analyzer circuit 222 may detect one or more characteristics from the cardiac electrical signal or cardiac mechanical signal. The response characteristics may indicate efficacy of stimulation of the heart, or a complication introduced by the stimulation. The response characteristics may include temporal or morphological features indicative of intrinsic cardiac activity such as a P wave, Q wave, R wave, QRS complex, or T wave that may be detected from a surface ECG, a subcutaneous ECG, or an intracardiac EGM. The response characteristics may include timing and intensity of evoked cardiac activity such as evoked electrical or mechanical activation in response to an electrostimulation of the heart. Examples of the intensity measure may include signal amplitude, slope or rate of change of signal amplitude, amplitude of a transformed physiological signal such as integrated signal, or a frequency-domain measurement such as power spectral density. The response characteristics may additionally or alternatively include relative measures computed from two sensed physiological signals, such as a timing delay between activations respectively detected from the signals sensed at two different cardiac sites. Examples of the signal analyzer circuit and response characteristics are discussed below, such as with reference to FIG. 3.

The therapy programmer circuit 230 may be in communication with the sensor circuit 220, and configured to determine at least first and second stimulation vectors and a therapy mode for use in multi-site stimulation according to the first and second stimulation vectors. The therapy programmer circuit 230 may be implemented as a part of a microprocessor circuit within the multi-site electrostimulation circuit 200. The microprocessor circuit may be a dedicated processor such as a digital signal processor, application specific integrated circuit (ASIC), microprocessor, or other type of processor for processing information including physical activity information. Alternatively, the microprocessor circuit may be a general purpose processor that may receive and execute a set of instructions of performing the functions, methods, or techniques described herein.

In an example such as illustrated in FIG. 2, the therapy programmer circuit 230 may include circuit sets comprising one or more other circuits or sub-circuits, that may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 2, the therapy programmer circuit 230 may include a stimulation vector selector circuit 231 and a therapy mode programmer circuit 232. The stimulation vector selector circuit 231 may use one or more of the response characteristics, such as generated by the signal analyzer circuit 222, to determine at least a first stimulation vector (hereinafter referred to as "LVa") for electrostimulation at a first LV site, and a second stimulation vector (hereinafter referred to as "LVb") for electrostimulation at a different second LV site. The LVa vector includes a first LV cathode and a first anode. The LVb vector includes a second LV cathode and a second anode. The first and second LV cathode may each be selected from electrodes on one or more LV leads, such as the LV electrodes 161-164 on the LV lead 108C. The first and second LV cathode may alternatively be selected from electrodes on a LV catheter, or one or more untethered pacing units each having at least one electrode positioned at the LV of the heart.

The stimulation vector selector circuit 231 may determine the LVa and LVb vectors from a plurality of candidate LV stimulation vectors $\{LV_k\}=\{LV_1, LV_2, \ldots, LV_N\}$. The candidate LV stimulation vectors may each include a LV cathode and an anode. Depending on the location of the anode, the candidate LV stimulation vectors may have unipolar, true bipolar, or extended bipolar configuration. A unipolar LV candidate vector may have an anode of the can housing 112 or a reference electrode on the can housing. A true bipolar LV candidate vector may have a LV anode different than the LV cathode of that vector. An extended bipolar LV candidate vector may have a LV anode of one of a RA electrode such as one of the electrodes 141 or 142, a RV electrode such as one of the electrodes 152-155, or electrodes on one or more leads, catheters, or untethered pacing units that are positioned at the RV, superior vena cava (SVC) or inferior vena cava (IVC), RA, or LA.

The stimulation vector selector circuit 231 may determine the LVa and LVb vectors sequentially. The LVa vector may first be determined when one or more response characteristics associated with the respective candidate LV stimulation vector satisfy a specified condition, such as to indicate effective stimulation of the heart with no or tolerable complications caused by the stimulation. The vector LVb may then be determined using the LVa, or together with one or more response characteristics associated with the respective candidate LV stimulation vectors. In some examples, a user may provide a configuration of LVa vector such as via the user interface 250, and the stimulation vector selector circuit 231 may determine LVb vector based at least on the user-provided LVa vector. In some examples, the stimulation vector selector circuit 231 may determine, in addition to the LVa and LVb vectors, other LV stimulation vectors or stimulation vectors for stimulating one or more other heart chambers (e.g., RA, RV, or LA). Examples of the stimulation vector selector circuit are discussed below, such as with reference to FIG. 3.

In some examples, the multi-site electrostimulation circuit 200 may comprise a memory circuit 260 to store information about spatial locations of electrodes. The information may include relative proximity among the electrodes, such as electrodes disposed at distal portion of the lead (e.g., LV electrodes 161 and 162 that are at or close to the distal tip of the LV lead 108C) or at proximal portion of the lead (e.g., LV electrodes 163 and 164 that are farther away from the tip of the LV lead 108C). The information may additionally or alternatively include lead type, lead design, or information about electrodes on a lead such as information about inter-electrode spacing along the lead, such as provided in a specification of the lead, which may be stored in the memory circuit 260. In some examples, the information about electrode spatial distribution may be obtained from medical images taken after the electrodes have been positioned on respective target sites, and in-situ electrode proximity or the inter-electrode distance may be measured or estimated. The stimulation vector selector circuit 231 may use the information about the spatial distribution of electrodes stored in the memory circuit 260, along with one or more response characteristics from the signal analyzer circuit 222, to determine the LVa vector. Examples of stimulation vector selection are discussed below, such as with reference to FIG. 3.

The therapy mode programmer circuit 232 may receive one or more response characteristics and the information about the LVa and LVb vectors and determine a therapy mode for multi-site stimulation. The therapy mode may include a first chronological order of delivering at least a first therapy such as a first LV stimulation according to the LVa vector and a second therapy such as a second LV stimulation according to the LVb vector. The first chronological order may indicate synchronization between the first and second stimulations. Examples of the first chronological order may include: the first LV stimulation preceding the second LV stimulation in time (denoted by "LVa→LVb"); the second LV stimulation preceding the first LV stimulation in time (denoted by "LVb→LVa"); or the first LV stimulation substantially simultaneously delivered with the second LV stimulation (denoted by "LVa|LVb"). In some examples, the therapy mode may include a first timing offset between the first and second LV stimulations for the chronological orders of "LVa→LVb" or ""LVb→LVa". The therapy mode may also include stimulation parameters including intensity, duration, or frequency of the first or second LV stimulation. The therapy mode programmer circuit 232 may determine the timing offset between the first and second LV stimulation, or the stimulation parameters for the first or second LV stimulation, using one or more of the response characteristics. Examples of the therapy mode programmer circuit are discussed below, such as with reference to FIG. 4.

The controller circuit 240 may receive programming input from the user interface 250 to control the operations of the electrostimulation circuit 210, the sensor circuit 220, the therapy programmer circuit 230, and the data flow and instructions between these components and respective subcomponents. In an example, the controller circuit 240 may configure the electrostimulation circuit 210 to deliver multi-site stimulation including at least the first and second LV stimulations according to the therapy mode such as determined by the therapy programmer circuit 230. In an example, the first and second LV stimulations may be delivered during the same cardiac cycle, simultaneously or separated by a timing offset less than a sensed or paced interval value of a cardiac cycle, such as determined by the therapy programmer circuit 230. In some examples, other therapies may be initiated or adjusted, including electrostimulation at non-cardiac tissues such as nerve tissues, or other types of therapies such as drug therapies, which may be used to restore cardiac function or prevent or slowdown the worsening of an existing cardiac disease such as heart failure.

The user interface 250 may include an input device that enables a system user to program the parameters used for electrostimulation or for sensing the physiological signals. Examples of the input device may include a keyboard, on-screen keyboard, mouse, trackball, touchpad, touchscreen, or other pointing or navigating devices. The input device may enable the system user to activate automated programming of multi-site stimulation, such as automated determination of the first and second stimulation vectors or the therapy mode including one or both of the chronological order and timing offset between the first and second stimulations delivered according to respective first and second stimulation vectors. The input device may also enable the system user to confirm or modify the automatically determined therapy programming, including one or more of the stimulation vector configurations and therapy mode.

The user interface 250 may include a display for presenting, in a human-perceptible medium format, multi-site stimulation programming such as automatically determined configurations of the stimulation vectors and the therapy mode including one or both of the chronological order and timing offset. The displayed information may also include information about device programming, device status such as lead impedance and integrity, battery status such as remaining lifetime of the battery, or cardiac stimulation threshold, or complications associated with stimulation at one or more cardiac sites, among others. The displayed information may be presented in a table, a chart, a diagram, or other textual, tabular, or graphical presentation formats. Examples of a user interface for multi-site stimulation are discussed below, such as with reference to FIG. 5.

Portions of the multi-site cardiac stimulation circuit 113 may be distributed between an ambulatory medical device such as the IMD 110 and an external programmer device such as the external system 120. In an example, the electrostimulation circuit 210 and the sensor circuit 220 may be included in the ambulatory medical device. At least a portion of the therapy programmer circuit 230 and the user interface unit 250 may be included in the external programmer circuit.

Figure 3:
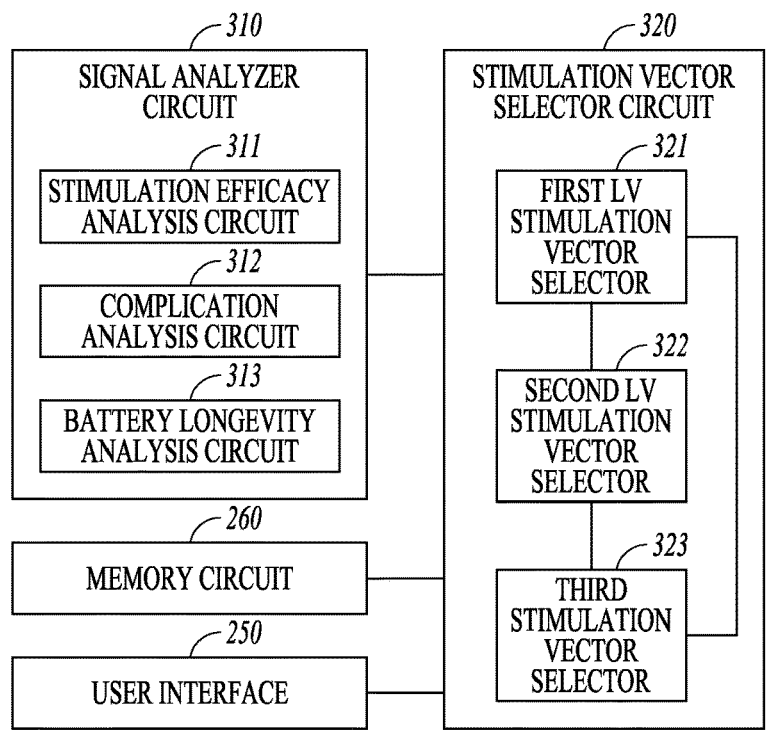
FIG. 3 illustrates generally an example of a stimulation vector selector circuit.

FIG. 3 illustrates generally an example of a stimulation vector selector circuit 320, which may be an embodiment of the stimulation vector selector circuit 230 in FIG. 2. The stimulation vector selector circuit 320 may include a first LV stimulation vector selector 321 to determine a first LV stimulation vector LVa, and a second LV stimulation vector selector 322 to determine a second LV stimulation vector LVb. In some examples, a user may provide a configuration of LVa vector such as via the user interface 250, and the stimulation vector selector circuit 320 may determine LVb vector based at least on the user-provided LVa vector. The stimulation vector selector circuit 320 may additionally include a third stimulation vector selector 323 to determine a third stimulation vector for electrostimulation at a third cardiac site different from the first and second LV sites.

The stimulation vector selector circuit 320 may be in communication with the signal analyzer circuit 310, which may be an embodiment of the signal analyzer circuit 222 in FIG. 2. The signal analyzer circuit 310 may include one or more of a efficacy analysis circuit 311, a complication analysis circuit 312, and a battery longevity analysis circuit 313. The stimulation efficacy analysis circuit 311 may generate one or more signal metrics from one or more cardiac electrical signals or cardiac mechanical signals sensed when the heart is stimulated according to a specified electrostimulation vector. Examples of signal metrics generated from the cardiac electrical signals may include: amplitude and timing of P wave, Q wave, R wave, QRS complex, or T wave detected from a surface ECG or a subcutaneous ECG; QRS width; amplitude and timing of activation of at least a portion of a chamber of the heart such as RA, RV, LA and LV, obtained from the intracardiac EGMs; cardiac stimulation threshold representing minimal stimulation intensity to produce a propagating cardiac depolarization; impedance sensed during electrostimulation; electrical delay of a chamber of the heart such as LV electrical delay; interventricular conduction delay measured as the delay between RV activation and LV activation (RV-LV) delay; intraventricular delay, among others. Examples of signal metrics generated from the cardiac mechanical signal metrics may include: intensity of a component of the sensed heart sound (HS) signal including one or more of first (S1), second (S2), third (S3), or fourth (S4) heart sounds; mechanical delay such as time intervals indicative of systole or diastole; pressures inside a heart chamber; end-systolic volume; or end-diastolic volume; among others. The signal metrics may additionally or alternatively include electromechanical metrics indicative of electromechanical coupling of the heart, which may include pre-ejection period (PEP), a systolic timing interval (STI), or a diastolic timing interval (DTI), among other cardiac timing intervals. The PEP represents the total duration of the electrical and mechanical events prior to ejection, and may be measured as the time duration from the onset of the QRS to the S1 heart sound, or the time duration from the ventricular pacing (Vp) signal to the beginning of ventricular ejection such as represented by the onset of S1 heart sound. The STI represents the duration of total electromechanical systole, and contains two major components, namely the PEP and the LVET. The STI may be measured as an interval from the onset of the QRS complex on the ECG or the atrial activation event in an intracardiac EGM to the S2 heart sound, or from the ventricular pacing (Vp)

signal to the end of ventricular ejection such as represented by the onset of S2 heart sound. The DTI represents the duration of total electro-mechanical diastole, and may be measured as the interval from the S2 heart sound to the onset of the QRS complex on the ECG or the atrial activation event in an intracardiac EGM of the next cardiac cycle.

Some signal metrics generated by the stimulation efficacy analysis circuit 311 may be predictive of patient hemodynamic response to the therapeutic cardiac electrostimulation. In an example, a Q-LV interval measured from Q wave of a surface ECG to local intrinsic activation at the LV stimulation site (such as detected as the first dominant peak on the LV electrogram) may be correlated to maximum rate of increase in LV pressure (LV dP/dt max, a clinical index to characterize the contractile ability of the heart), thus indicative of LV contractility. Q-LV interval therefore may be used to assess efficacy of the LV electrostimulation therapy delivered using a specified pacing vector. In another example, intensity of S1 heart sounds (such as S1 amplitude) may be correlated to LV dP/dt max, thus indicative of the LV contractility. In another example, the mechanical delay may include left-ventricular ejection time (LVET), an interval from the opening to the closing of the aortic valve (mechanical systole). The LVET may be correlated to hemodynamic of the LV, and may be measured as an interval between S1 and S2 heart sound within the same cardiac cycle. S1 intensity and LVET therefore can each be used to assess efficacy of the LV electrostimulation therapy delivered using a specified pacing vector.

The complication analysis circuit 312 may be configured to detect a complication indicator indicating non-cardiac activation produced by the electrostimulation to the heart according a specified electrostimulation vector. The complication indicator may include one or more indications of extra-cardiac stimulation or non-cardiac muscle stimulation, such as stimulation of skeletal muscle, diaphragm, phrenic nerve stimulation (PNS), unintended nerve stimulation, anodal cardiac stimulation, or any other parameters that do not support intended cardiac therapeutic effect. The unintended nerve or skeletal muscle stimulation may be caused by excessive energy delivered to the heart such as due to a high capture threshold, or close proximity between the cardiac stimulation electrode and the nerves or the skeletal muscle. In an example, the complication analysis circuit 312 may be coupled to an accelerometer sensor configured to sense skeletal muscle activation in response to the cardiac electrostimulation delivered using a specified electrostimulation vector. In another example, the complication analysis circuit 312 may be coupled to a microphone sensor or an electromyogram (EMG) sensor to detect an activation of the laryngeal muscles, such as coughing response to undesirable activation of the laryngeal muscles or nerves caused by the electrostimulation delivered using a specified electrostimulation vector.

In an example, the complication analysis circuit 312 may detect the phrenic nerve activation using an accelerometer or other sensors during delivery of cardiac electrostimulation. The presence or absence of phrenic nerve activation in response to the electrostimulation may be detected by comparing the accelerometer signal intensity to a specified threshold value. Detection of the phrenic nerve activation can also include determining one or more parameters including a phrenic nerve stimulation threshold ($PNS_T$) representing minimum stimulation energy sufficient to elicit phrenic nerve activation, or a safety margin for phrenic nerve activation such as determined as a difference of between $PNS_T$ and the cardiac stimulation threshold.

The complication analysis circuit 312 may determine the phrenic nerve activation parameters (such as $PNS_T$) by delivering electrostimulation using a specified electrostimulation vector. The energy delivered may also be used to simultaneously search for a cardiac stimulation threshold. If no phrenic nerve activation is sensed using the stimulation energy delivered, the energy level may be increased in subsequent trials of electrostimulation, until phrenic nerve activation is detected. Alternatively, if phrenic nerve activation is sensed using the stimulation energy delivered, the level of stimulation energy may be decreased until phrenic nerve activation is not detected.

The battery longevity analysis circuit 313 may be configured to generate a battery longevity indicator indicating a battery status such as projected remaining lifetime of the battery. Battery longevity may be affected by a number of factors, including battery chemistry and battery voltage and impedance, configuration of electrostimulation vectors, polarity and number of electrodes that form a stimulation vector, lead impedance, capture threshold indicative of minimum amount of energy required to generating a propagating cardiac depolarization, mode or sequence of electrostimulation which determines the "ON" time for delivery of electrostimulation, stimulation parameters including pulse amplitude, pulse width, frequency, duty cycle, among others. In one example, the battery longevity may be estimated using a model of battery capacity and expected circuit performance, such as described by Russie, in U.S. Pat. No. 7,620,452, entitled "SYSTEMS AND METHODS FOR MANAGING THE LONGEVITY OF AN IMPLANTABLE MEDICAL DEVICE BATTERY," which is herein incorporated by reference in its entirety. In another example, the longevity may be calculated based on sensed capacity as measured by a coulometer or a capacity-by-voltage device, such as described by Gandhi et al. in U.S. Pat. No. 8,055,343, entitled "DYNAMIC BATTERY MANAGEMENT IN AN IMPLANTABLE DEVICE," which is herein incorporated by reference in its entirety.

The first LV stimulation vector selector 321 may determine the first LV stimulation vector (LVa) from a plurality of candidate LV stimulation vectors $\{LV_k\}=\{LV_1, LV_2, \ldots, LV_N\}$. Each candidate LV stimulation vector may include a LV cathode and an anode. The LV cathode may be selected from electrodes on one or more LV leads or catheters, such as the LV electrodes 161-164 on the LV lead 108C, or one or more untethered pacing units each having at least one electrode positioned at the LV of the heart. The anode of the candidate LV stimulation vectors may include a can housing electrode, a RV electrode, a RA or LA electrode, a SVC or IVC electrode, or a different LV electrode.

The first LV stimulation vector (LVa) may be selected when one or more response characteristics satisfying a specified condition. The response characteristics may include one or more stimulation efficacy indicators, complication indicators, or battery longevity indicators in response to the electrostimulation delivered according to the candidate LV stimulation vectors. In an example, the first LV stimulation vector selector 321 may screen the plurality of candidate LV stimulation vectors to identify a first set of candidate LV stimulation vectors each having substantially no PNS indication, such as when a $PNS_T$ or a safety margin (between LV stimulation threshold and the $PNS_T$) exceeds a respective threshold. Because PNS may cause hiccups which may interfere with normal breathing and the intended therapeutic effect of the cardiac electrostimulation, stimulation vector associated with no phrenic nerve activation, a higher $PNS_T$, or a larger safety margin between the LV stimulation threshold and the $PNS_T$ may be generally preferred in cardiac stimulation. In some examples, the screening may additionally include eliminating from the first set of the candidate LV stimulation vectors those stimulation vectors associated with stimulation impedance measurements outside a specified range, such as outside a range of approximately 200-3000 ohms. The screening may additionally include eliminating from the first set those LV stimulation vectors with missing data or substantial amount of loss of capture during LV threshold testing.

The first LV stimulation vector selector 321 may further select, from the first set of candidate LV stimulation vectors, a second set of stimulation vectors each having a RV–LV delay satisfying a specified condition. The RV–LV delay may be measured as timing difference between activations at a LV site and a RV site during intrinsic cardiac rhythm or in response to a stimulation of at RV or RA of the heart. A positive RV–LV delay indicates a delayed LV activation subsequent to a RV activation, and a negative RV–LV delay indicates a delayed RV activation subsequent to a LV activation. In an example, the second set may include the LV stimulation vectors associated with substantially longer RV–LV delay than other of the first set of candidate LV stimulation vectors. For example, if RV–LV delays of the candidate LV stimulation vectors all have positive values, then the LV stimulation vector(s) with the largest RV–LV value are included in the second set. If RV–LV delays of the candidate LV stimulation vectors all have negative values, then the LV stimulation vector(s) with the largest RV–LV value (or equivalently, smallest absolute value of RV-LV delay) are included in the second set. If RV–LV delays of the candidate LV stimulation vectors include both positive and negative values, then the LV stimulation vector(s) with the largest positive RV–LV value are included in the second set.

If only one LV stimulation vector is selected in the second set, then that only one vector may be determined to be the vector LVa. If more than one vector is associated with substantially identical RV–LV delay (such as the difference of RV-LV delays associated with different stimulation vectors within a specified margin) and thus included in the second set, then the vector LVa may be determined to be the one corresponding to a substantially smaller LV stimulation threshold than other of the second set of candidate LV stimulation vectors. In some examples, the first LV stimulation vector selector 321 may compute, for each of the candidate LV stimulation vectors, a respective composite response characteristic using two or more response characteristics selected from the stimulation efficacy indicators, the complication indicators, or the battery longevity indicators. The composite response characteristic may indicate an overall performance of a candidate LV stimulation vector. By way of non-limiting example, the composite response characteristic may be computed as a weighted combination, or other linear or nonlinear combinations, of the stimulation impedance, the RV–LV delay, and the LV stimulation threshold. The LVa vector may be determined as the vector with the corresponding composite response characteristic satisfying a specified condition, such as being greater than the composite response characteristics of other candidate LV stimulation vectors.

The second LV stimulation vector selector 322 may determine the second LV stimulation vector (LVb) that includes a second LV cathode and a second anode. The second LV stimulation vector selector 322 may compare the cathodes of the plurality of candidate LV stimulation vectors $\{LV_k\}$ to the cathode of the vector LVa that has been determined by the first LV stimulation vector selector 321, and determine the second cathode of the vector LVb to be the one that is spatially more distant from the cathode of the LVa vector than other of the LV cathodes of the plurality of candidate LV vectors. Information about lead type, lead design, or information about electrodes on a lead such as spatial distance or relative proximity among the electrodes may be retrievably stored in the memory circuit 260 and made available to the second LV stimulation vector selector 322. By way of non-limiting example, cathodes of the candidate LV stimulation vectors may be one of the electrodes 161-164 on the LV lead 108C as illustrated in FIG. 1. If electrode 161 is selected as the cathode for the vector LVa, the second LV stimulation vector selector 322 may determine electrode 164 to be the cathode for the vector LVb if the electrode 164 is spatially more distant from the electrode 161 than other electrodes 162 and 163.

The second LV stimulation vector selector 322 may determine the vector LVb from a third set of candidate LV stimulation vectors each having the second LV cathode. The determination of LVb may be based on one or more of response characteristics generated by the signal analyzer circuit 310, such as one or more of the stimulation efficacy indicators, complication indicators, or battery longevity indicators. In an example, the LVb is determined as the LV stimulation vector associated with a substantially smaller LV stimulation threshold than other of the third set of candidate LV stimulation vectors. By way of non-limiting example, the third set of candidate LV stimulation vectors all have cathode electrode 164 and anodes being one of a RV electrodes 152-155, RA electrodes 141-142, or the can housing 112. The second LV stimulation vector selector 322 may compare the LV stimulation thresholds corresponding to the candidate LV stimulation vectors in the third set, and determine the LVb vector including the cathode electrode 164 and anode electrode 154 if a smaller stimulation threshold is produced when the heart is stimulated according to LVb than according to any other stimulation vector including the cathode electrode 164 and an anode different than the electrode 154. In another example, the LVb is determined as the LV stimulation vector associated with lower power or current consumption, and accordingly longer projected device longevity, than other of the third set of candidate LV stimulation vectors. The current consumption may be estimated using the LV stimulation threshold ($V_T$), stimulation impedance (Z), and the pulse width (PW) of the stimulation pulse, such as computed as $PW*V_T/Z$. If PW is a constant for stimulations delivered according to the third set of candidate LV stimulation vectors, the LVb may be determined as the LV stimulation vector associated with the smallest $V_T/Z$ value.

In various examples, information about the spatial distance or relative proximity among LV electrodes may be specific to a particular type of lead or a particular lead design. The lead-specific information, such as information about electrodes on a lead, either retrievably stored in the memory circuit 260 or provided by a user such as via the user interface 250, may be used by the second LV stimulation vector selector 322 to determine the LVb vector. In an example, the electrodes on the LV lead or catheter may include a distal LV electrode and two or more proximal LV electrodes on the lead, where the distal LV electrode has an inter-electrode distance (away from any proximal LV electrode) substantially greater than inter-electrode distance among the two or more proximal LV electrodes. If the cathode of the vector LVa is determined as one of the proximal LV electrodes, then the second LV stimulation vector selector 322 may determine the cathode of the vector LVb as the distal electrode. The second LV stimulation vector selector 322 may select, from the set of candidate LV stimulation vectors each having a cathode as the distal LV electrode, the vector LVb that has the lowest LV stimulation threshold. If the cathode of the vector LVa is determined to be the distal LV electrode, then the second LV stimulation vector selector 322 may compare the LV stimulation thresholds associated with a set of candidate LV stimulation vectors each having a cathode being one of the proximal LV electrodes. The second LV stimulation vector selector 322 may determine the vector LVb to be the vector that is associated with the lowest LV stimulation threshold among the candidate LV stimulation vectors.

In an example, the electrodes on the LV lead or catheter include a plurality of distal electrodes and a plurality of proximal electrodes, and the distal and proximal electrodes are substantially equally spaced along the lead. If the cathode of the vector LVa is determined as one of the proximal LV electrodes, then the second LV stimulation vector selector 322 may compare the LV stimulation thresholds associated with a first set of candidate LV stimulation vectors each having a cathode being one of the distal LV electrodes. The LVb vector may be determined to be the vector associated with substantially smaller LV stimulation threshold than other of the first set of candidate LV stimulation vectors. If the cathode of the vector LVa is determined as one of the distal LV electrodes, then the second LV stimulation vector selector 322 may compare the LV stimulation thresholds associated with a second set of candidate LV stimulation vectors each having a cathode being one of the proximal LV electrodes. The second LV stimulation vector selector 322 may determine the vector LVb to be the vector associated with a substantially smaller LV stimulation threshold than other of the second set of candidate LV stimulation vectors.

In an example, the second LV stimulation vector selector 322 may determine the LVb vector based on "in-situ" electrode proximity or the inter-electrode distance, such as measured form a medical image taken after the electrodes have been positioned on respective target sites. By way of non-limiting example, if the cathode of the LVa vector is selected to be an electrode positioned towards a basal region of the heart, then the cathode of the LVb vector may be selected to be an electrode positioned towards an apical region of the heart. Conversely, if the cathode of the LVa vector is selected to be an electrode positioned towards an apical region of the heart, then the cathode of the LVb vector may be selected to be an electrode positioned towards a basal region of the heart.

In an example, the second LV stimulation vector selector 322 may determine the LVb vector further using a specified priority of the LV cathodes or a specified priority of anodes. The specified priority may be pre-determined and stored in the memory circuit 260, or be provided by the system user via the user interface 250. By way of non-limiting example, four LV electrodes (E1-E4) may be included on a LV lead, where E1 is the most distal (or apical) electrode and E4 the most proximal (or basal) electrode. In an example, electrodes E1 to E4 correspond to, respectively, electrodes 161-164 on the LV lead 108C. The second LV stimulation vector selector 322 may determine the cathode for LVb vector according to a priority as provided in Table 1 below. For example, if the most proximal electrode E4 is chosen as the cathode of LVa vector, then electrode E1 has a higher priority over E2, which has a higher priority over E3, to be selected as the cathode of the vector LVb. In another example, if the most distal electrode E1 is chosen as the cathode of LVa vector, then the priority of the cathodes may be determined, in addition to the relative spatial proximity among the electrodes E2-E4, further using LV stimulation thresholds associated with electrostimulation of the heart according to the LV stimulation vectors that include the respective cathodes. For example, as illustrated in Table 1, if E4 corresponds to a LV stimulation threshold that is lower than or substantially identical to that of E3, then E4 is preferred over E3, which is preferred over E2, to be used as the cathode of the LVb vector. However, if E3 corresponds to a LV stimulation threshold lower than that of E4, then E3 is preferred over E4, which is preferred over E2, to be used as the cathode of the LVb vector.

TABLE 1

Prioritized cathode selection for the LVb vector.

| Cathode of LVa | Priority of cathodes of LVb |
|---|---|
| E4 | E1 > E2 > E3 |
| E3 | E1 > E4 > E2 |
| E2 | E1 > E4 > E3 |
| E1 | (1) E4 > E3 > E2, if E4 corresponds to a lower, or substantially identical, LV stimulation threshold than E3; or (2) E3 > E4 > E2, if E3 corresponds to a lower LV stimulation threshold than E4. |

The second LV stimulation vector selector 322 may determine the LVb vector using a specified priority of anodes, such as when two or more LV stimulation vectors in the third set of candidate LV stimulation vectors (each having the second LV cathode) have substantially identical LV stimulation threshold, such as the difference being within a specified margin. In an example, a descending order of anodes priority may be represented by $E_{RVx} > E_X >$ can housing, indicating an electrode on the RV ($E_{RVx}$) is preferred over an electrode on the LV that is different than the selected cathode of the LVb vector ($E_X$), which is preferred over the can housing electrode. In another example, if the most distal LV electrode E1 is selected to be the cathode of the LVb vector, a descending order of anode priority may be represented as $E_{RVx} > E4 > E3 > E2 >$ Can housing.

The third stimulation vector selector 323 may be configured to determine a third stimulation vector for electrostimulation at a third cardiac site different from the first and second LV sites. In an example, the third cardiac site may include a right ventricular (RV) site, and the third stimulation vector is a RV stimulation vector RVx that includes a RV cathode and an anode. The RV cathode may be selected from electrodes on one or more RV leads or catheters, such as the electrodes 153-154 on the RV lead 108B, or one or more untethered pacing units each having at least one electrode positioned at the RV of the heart. The anode of the RVx vector may include a can housing electrode, a RV electrode different than the RV cathode, a LA or RA electrode, or a SVC or IVC electrode, among others. In an example, the RVx vector may have a predetermined configuration, with a cathode being the tip electrode 152 and an anode being the ring electrode 153. In an example, the stimulation vector selector circuit 320 may receive a selection, such as via the user interface 250, between a multi-site biventricular stimulation of both LV sites and RV sites ("BiV"), or a multi-site LV stimulation of various LV sites. The third stimulation vector selector 323 may generate the RVx vector when the multi-site BiV stimulation is selected.

Figure 4:
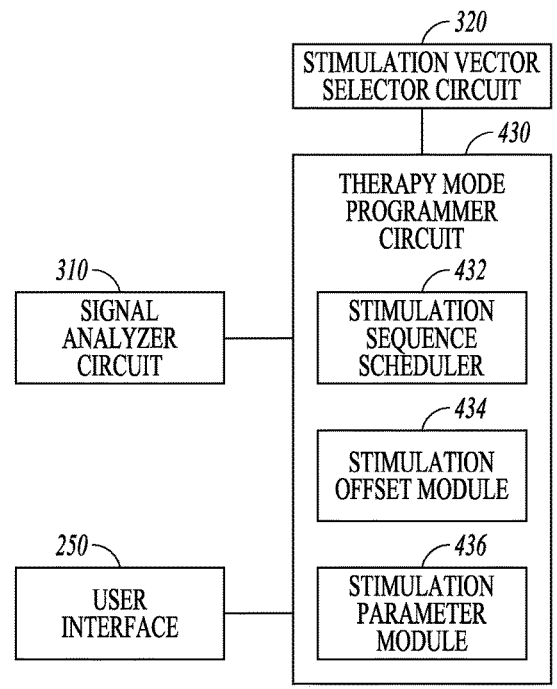
FIG. 4 illustrates generally an example of a therapy mode programmer circuit.

FIG. 4 illustrates generally an example of a therapy mode programmer circuit 430, which may be an embodiment of the therapy mode programmer circuit 232 in FIG. 2. The therapy mode programmer circuit 430 may be coupled to the stimulation vector selector circuit 320 to determine mode of delivery of stimulations according to the stimulation vectors such as determined by the stimulation vector selector circuit 320. The therapy mode programmer circuit 430 may include one or more of a stimulation sequence scheduler 432, a stimulation offset module 434, and a stimulation parameter module 436, each of which may determine a particular parameter of the therapy mode.

The stimulation sequence scheduler 432 may determine, for the first stimulation vector LVa and the second stimulation vector LVb such as selected by the stimulation vector selector circuit 320, a chronological order between a first LV stimulation delivered according to the LVa vector and a second LV stimulation delivered according to the LVb vector. Examples of the chronological order may include the first LV stimulation preceding the second LV stimulation in time, denoted by "LVa→LVb"; the second LV stimulation preceding the first LV stimulation in time, denoted by "LVb→LVa"; or the first LV stimulation substantially simultaneously delivered with the second LV stimulation, denoted by "LVa|LVb". The stimulation sequence scheduler 432 may be coupled to the signal analyzer circuit 310 and determine the chronological order using one or more response characteristics obtained from the physiological signals. In an example, the chronological order may be determined based on cardiac activations at the first and second LV sites, such as when the heart undergoes a specified intrinsic rhythm such as sinus rhythm or when the heart is stimulated according to a specified stimulation protocol such as RA pacing. Activation timings may be computed as a time interval between a detected cardiac activation and a reference time. Examples of the reference time may include timing of a Q wave, timing of a sensed or paced activation at a location in the heart such as the RV within the same cardiac cycle as the activations at the first and second LV sites, or timing of the stimulation that evokes the physiological responses. In an example, the reference time may include timing of a sensed or paced activation at a RV site sensed within the same cardiac cycle as the activations at the first and second LV sites. The activation timings may include a first activation delay ($\Delta Ta$) between the activation at the first LV site and the RV activation, and a second activation delay ($\Delta Tb$) between the activation at the second LV site and the RV activation.

The activation timings sensed at the first and second LV sites may be compared to each other to determine the chronological order of delivering the first and second stimulations. In an example, if the first activation delay $\Delta Ta$ is substantially greater than the second activation delay $\Delta Tb$, it indicates that the first LV site is activated later in time than the second LV site. The chronological order may then be determined to be "LVa→LVb", that is, the first LV stimulation according to the LVa vector may precede the second LV stimulation according to the LVb vector. If the first activation delay $\Delta Ta$ is substantially no greater than the second activation delay $\Delta Tb$, then a chronological order "LVa|LVb" may be determined, that is, the first LV stimulation according to the LVa vector may be delivered substantially simultaneously with the second LV stimulation according to LVb vector.

In some examples, if a multi-site biventricular stimulation of both LV sites and RV sites ("BiV") is selected such as by a system user via the user interface 250 and if a third stimulation vector such as a RV stimulation vector RVx is selected by the stimulation vector selector circuit 320, the stimulation sequence scheduler 432 may additionally determine a second chronological order between a third cardiac stimulation delivered according to the third stimulation vector (such as the RVx vector) and the first or second LV stimulation. In an example, the signal analyzer circuit 310 may measure from the sensed physiological signal a LV activation (such as at the first or second LV site) and a RV activation within the same cardiac cycle, and determine a RV–LV delay that is measured from the detected LV activation to the detected RV activation. The stimulation sequence scheduler 432 may determine the second chronological order based at least on the RV–LV delay. In an example, if the RV-LV activation delay exceeds a specified threshold (such as approximately 20 milliseconds), then the first and second LV stimulations may precede the third cardiac stimulation such as according to the RVx vector, denoted by "(LVa, LVb)→RVx", where (LVa, LVb) may be one of the chronological orders of LVa→LVb, LVb→LVa, or LVa|LVb as previously discussed. If the RV–LV delay falls below the specified threshold, then the third cardiac stimulation such as according to the RVx vector may precede the first and second LV stimulations, denoted by "RVx→(LVa, LVb)".

The stimulation offset module 434, coupled to the stimulation vector selector circuit 320, may determine a first timing offset ($D_{LVa-LVb}$) between the first and second LV stimulation using one or more of the response characteristics generated by the signal analyzer circuit 310. In an example, the timing offset $D_{LVa-LVb}$ may be determined based on the activation timings at the first and second LV sites, such as the first activation delay $\Delta Ta$ between the activation at the first LV site and the RV activation and the second activation delay $\Delta b$ between the activation at the second LV site and the RV activation. If $\Delta Ta$ is substantially greater than $\Delta Tb$, then corresponding to the chronological order "LVa→LVb", the stimulation offset module 434 may determine a first timing offset proportional to a difference between $\Delta Ta$ and $\Delta Tb$, that is:

$$D_{LVa-LVb}=k \cdot (\Delta Ta - \Delta Tb)$$

where k is a positive scaling factor. In an example, the scaling factor k may take a value between 0 and 1. If $\Delta Ta$ is substantially no greater than $\Delta Tb$, then corresponding to the chronological order "LVa|LVb" (i.e., substantially simultaneous delivery of the first and second stimulations), the stimulation offset module 434 may determine the timing offset $D_{LVa-LVb}=0$.

When a multi-site biventricular stimulation of both LV sites and RV sites ("BiV") is selected and if a third stimulation vector such as a RV stimulation vector RVx is selected by the stimulation vector selector circuit 320, the stimulation offset module 434 may additionally determine a second timing offset ($D_{LV-RV}$) corresponding to the second chronological order between a third cardiac stimulation according to the RVx vector and the first or second LV stimulation that is determined by the stimulation sequence scheduler 432. In an example, if the RV–LV delay exceeds a specified threshold (such as approximately 20 milliseconds), then corresponding to the chronological order of "(LVa, LVb)→RVx", the stimulation offset module 434 may determine the second timing offset $D_{LV-RV}$ proportional to a the RV–LV delay. Similarly, if the RV–LV delay falls below the specified threshold, then corresponding to the chronological order of "RVx→(LVa, LVb)", the stimulation offset module 434 may determine the second timing offset $D_{LV-RV}$ proportional to the RV–LV delay.

The stimulation parameter module 436 may be configured to determine one or more stimulation parameters for the first and second LV stimulation according to the respective vectors of LVa or LVb, or additionally for the third stimulation such as according to the RVx vector. Examples of the stimulation parameters may include amplitude, pulse width, duty cycle, duration, or frequency, among other parameters affecting the stimulation intensity or the energy delivered. The stimulation parameter module 436 may be coupled to the signal analyzer circuit 310 and determine the stimulation parameters using one or more response characteristics generated from the physiological signal. In an example, for the first or second stimulations according to the respective vectors LVa and LVb, one or more of the stimulation parameters may be determined based on the LV stimulation threshold at the first or second LV site, and the PNS threshold or a safety margin between the PNS threshold and the cardiac stimulation threshold. In various examples, different safety margins may be selected for the first and second stimulations associated with the LVa or LVb vectors to allow adequate cardiac stimulation and minimize or eliminate PNS. By way of non-limiting example, if the LVa vector is associated with a LV stimulation threshold of 0.5 volt, then the amplitude of the first LV stimulation according to the LVa vector may be set to 1.5 volt, i.e., a 1 volt safety margin added to the LV stimulation threshold. Alternatively, the first LV stimulation may have pulse amplitude determined through an automated threshold test. If the LVb vector is associated with a LV stimulation threshold of 2 volt, then the amplitude of the second LV stimulation according to the LVa vector may be set to 3.5 volt, i.e., a 1.5 volt safety margin added to the LV stimulation threshold of 2 volt.

One or more parameters of the therapy mode as determined by the therapy mode programmer circuit may be presented to a system user such as via the user interface 250. The user may use input devices associated with the user interface 250 to confirm, reject, or otherwise edit one or more of the chronological orders, timing offsets between the stimulations corresponding to the determined chronological order, or the stimulation parameters associated with one or more stimulation vectors.

Figure 5:
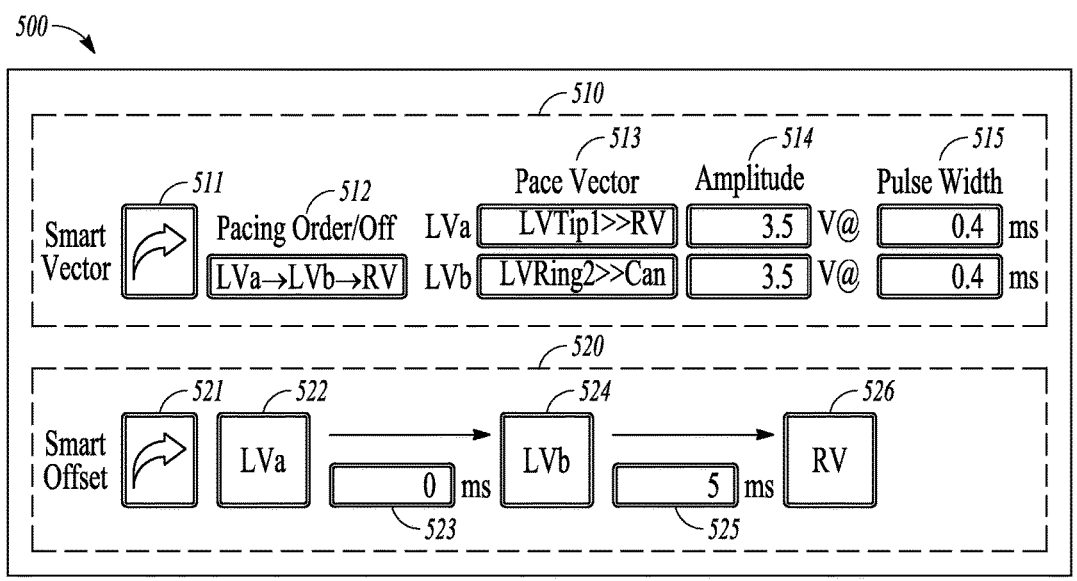
FIG. 5 illustrates generally an example of a portion of a user interface for programming therapy mode of multisite stimulation.

FIG. 5 illustrates generally an example of a portion of a user interface 500 for programming therapy mode of multisite stimulation. The user interface 500, which may be an embodiment of the user interface 250, may include display of a plurality of control elements and textual or graphical representations. The control elements may be shown as icons or bitmaps, optionally associated with text labels or markers indicating the function or manner of operation of the corresponding control elements. The control elements may include checkboxes, push buttons, radio buttons, or other user interface controls located on the display screen.

As illustrated in FIG. 5, the control elements may include a first zone 510 and a second zone 520. The first zone 510 may include a control element 511 (such as a push button) that enables a user to activate automatic selection of the stimulations vectors (such as executed by the stimulation vector selector circuit 320) and to activate automatic determination of chronological order between stimulations according to the selected stimulation vectors (such as executed by the stimulation sequence scheduler 432). Upon receiving a user command (such as push down of the control element 511), the first zone 510 may display the chronological order 512 of the multi-site stimulations according to two or more stimulation vectors, such as the chronological order "LVa→LVb→RV" as determined by the stimulation sequence scheduler 432, and the configurations 513 of the selected stimulation vectors such as LVa and LVb vectors, as determined by the stimulation vector selector circuit 320. The stimulation vector configuration 513 is presented as "cathode>>anode" format. For example, the "LVTip1>>RV" for LVa vector indicates the cathode being a distal tip electrode on the LV lead (such as electrode 161 on the LV lead 108C) and the anode being a RV electrode. The first zone 510 may also display the stimulation parameters associated with each of the selected stimulation vectors, such as amplitude 514 and pulse width 515, among other stimulation parameters such as determined by the stimulation parameter module 436.

The second zone 520 may include a control element 521 (such as a push button) that enables a user to activate automatic determination of timing offsets between stimulations delivered according to the selected stimulation vectors (such as executed by the stimulation offset module 434). By way of non-limiting example, the second zone 520 includes a display of the selected stimulation vectors including the LVa vector 522, the LVb vector 524, and the RV vector 526 arranged in a sequence consistent with the chronological order 512. The timing offset 523 between the stimulation vectors LVa and LVb, and the timing offset 525 between the stimulations vectors LVb and RV may also be displayed.

Various elements shown in the first zone 510 or the second zone 520 may be edited by the user via an input device. In an example, one or more of the chronological orders 512, the stimulation vector configurations 513, the stimulation parameters 514 and 515, or the timing offsets 523 and 525 may be displayed in an editable text box or a drop-down menu. The user may enter desired values in the text box, use the control buttons to increment or decrement the exiting value shown in the text box, or select desired values from a drop-down menu that includes a list of pre-stored values. Examples of the input device may include a keyboard, an on-screen keyboard, a mouse, a trackball, a touchpad, a touch-screen, or other on-screen selection and control means.

Figure 6:
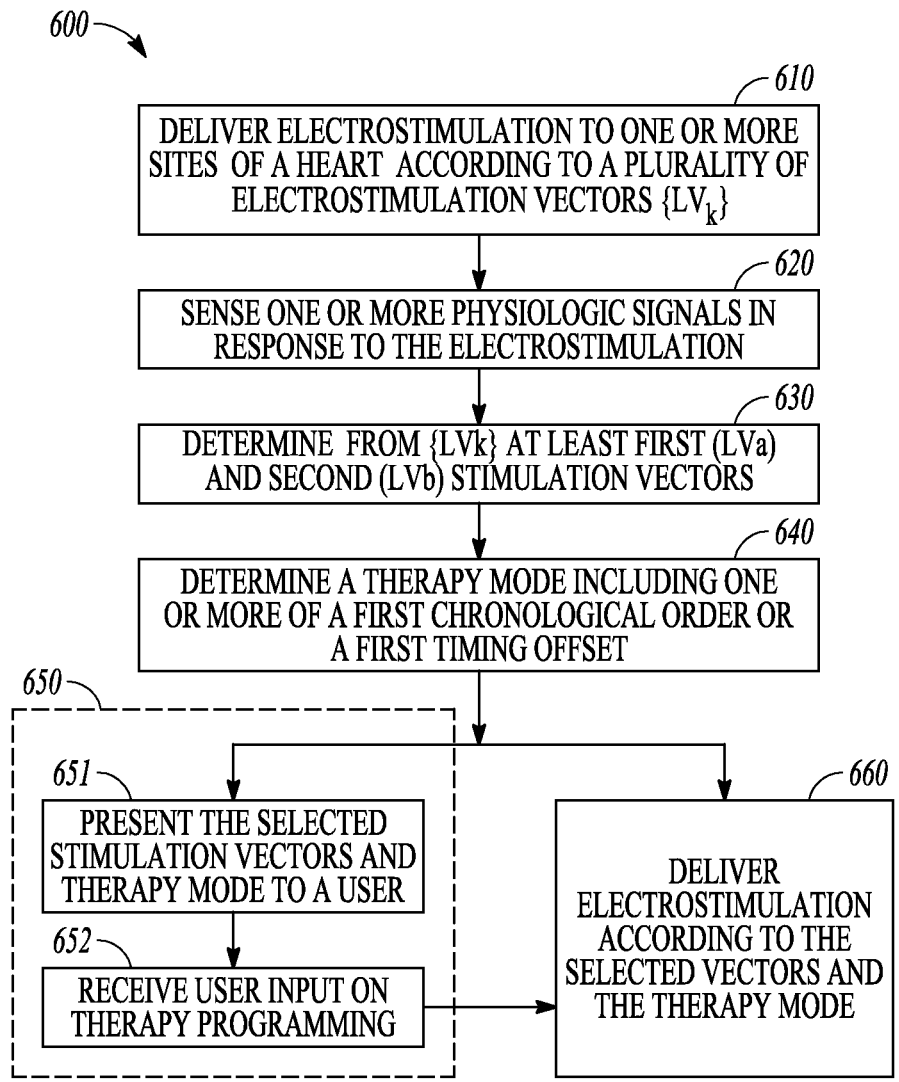
FIG. 6 illustrates generally an example of a method for programming multi-site electrostimulation such as for use in therapeutic stimulation of at least one chamber of a heart.

FIG. 6 illustrates generally an example of a method 600 for programming multi-site electrostimulation such as for use in therapeutic cardiac stimulation of at least one heart. The method 600 may be implemented and executable in an implantable, wearable, or other ambulatory medical device, a programmer for programming an implantable device, or a remote patient management system. In an example, the method 600 may be performed by the multi-site electrostimulation circuit 200, or any modification thereof.

The method 600 begins at step 610 by delivering electrostimulation to one or more sites in at least one chamber of a heart according to a plurality of candidate LV stimulation vectors $\{LV_k\}=\{LV1, LV2, \ldots, LV_N\}$. Each candidate electrostimulation vector comprises an anode and a cathode, and the electrostimulation may be delivered between the anode and the cathode. The electrostimulation can comprise one or more pulses generated by an implantable, wearable, or ambulatory pulse generator, or an external electrostimulation device. In an example, the electrostimulation may be delivered to one or more sites at the left ventricle (LV) of the heart, using each of a plurality of LV electrostimulation vectors. At least one of the anode or the cathode of each LV electrostimulation vector may be a LV electrode positioned at a site of LV of the heart. In an example, the LV electrostimulation vectors can include at least one unipolar LV electrostimulation vector involving a LV electrode and a reference electrode such as the IMD can 112. In another example, the LV electrostimulation vectors can include at least a bipolar LV electrostimulation vector involving two LV electrodes, a LV electrode and a RV electrode, or a LV electrode and a RA electrode.

At 620, one or more physiologic signals may be sensed such as by using an implantable, wearable, or other ambulatory sensor. The physiological signals may include cardiac electrical signals such as electrocardiograms (ECGs), intracardiac electrograms (EGMs), or cardiac mechanical signals indicative of activities such as contractions of an atrium or a ventricle. The one or more physiological signals may be sensed when the heart an intrinsic rhythm such as a sinus rhythm, or when the heart is stimulated in accordance with a specified stimulation protocol. In some examples, two or more physiological signals (such as EGMs) may be simultaneously or sequentially sensed from different sites on or within a heart chamber such as a left ventricle (LV).

One or more response characteristics may be detected from the cardiac electrical signal or cardiac mechanical signal at 620. The response characteristics may indicate efficacy of stimulation of the heart, or any complications introduced by the stimulation. The response characteristics may include temporal or morphological features indicative of intrinsic cardiac activity such as a P wave, Q wave, R wave, QRS complex, or T wave that may be detected from a surface ECG, a subcutaneous ECG, or an intracardiac EGM. The response characteristics may include timing and intensity of evoked cardiac activity such as evoked electrical or mechanical activation in response to an electrostimulation of the heart, or relative timing delay between activations respectively detected from the signals sensed at two different cardiac sites.

At 630, at least a first stimulation vector (LVa) for electrostimulation at a first LV site and a second stimulation vector (LVb) for electrostimulation at a different second LV site may be determined. The LVa and LVb vectors may be selected from the candidate vector set $\{LV_k\}$. The LVa vector includes a first LV cathode and a first anode. The LVb vector includes a second LV cathode and a second anode. The first and second LV cathode may each be selected from electrodes on one or more LV leads, such as the LV electrodes 161-164 on the LV lead 108C. The first and second LV cathode may alternatively be selected from electrodes on a LV catheter, or one or more untethered pacing units each having at least one electrode positioned at the LV of the heart.

The determination of the LVa and LVb vectors may be based on one or more of the response characteristics derived from the physiological signals at 620. The LVa and LVb vectors sequentially, such that the LVa vector may be determined first when one or more response characteristics associated with the respective candidate LV stimulation vector satisfy a specified condition, such as to indicate effective stimulation of the heart with no or tolerable complications caused by the stimulation. The identified LVa may then be used, such as together with one or more response characteristics associated with the respective candidate LV stimulation vectors, to determine a vector LVb. In some examples, the LVa vector may be provided by a system user, and at 620 the LVb vector may be determined based at least on the user-provided LVa vector. Examples of methods for determining the LVa and LVb vectors are discussed below, such as with reference to FIG. 7.

At 640, a therapy mode may be determined for multi-site stimulation. The therapy mode may include one or more of a first chronological order or a first timing offset, such as between a first therapy such as a first LV stimulation according to the LVa vector and a second therapy such as a second LV stimulation according to the LVb vector. The therapy mode may additionally include stimulation parameters respectively determined for the first and second LV stimulations. The stimulation parameters are used to determine intensity, duration, or frequency of the first or second LV stimulation. The timing offset between the first and second LV stimulations according to LVa and LVb, or the stimulation parameters for the first or second LV stimulation, may be determined based on one or more of the response characteristics. Examples of programming therapy mode for the selected stimulation vectors are discussed below, such as with reference to FIG. 8.

Information about the selected stimulation vectors LVa and LVb and the therapy mode may be utilized in one or more processes including information presentation, therapy recommendation, or automatic or confirmatory therapy delivery. At 651, multi-site stimulation programming such as automatically determined configurations of the stimulation vectors, and the therapy mode including one or both of the chronological order and timing offset may be presented on a display, such as on the user interface 250. Other information may also be displayed, including device programming, device status such as lead impedance and integrity, battery status such as remaining lifetime of the battery, or cardiac stimulation threshold, complications associated with stimulation at one or more cardiac sites, among others. At 652, user input on the therapy programming, including confirmation or modification of the automatically determined stimulation vector configurations and therapy modes, or activation of the automated programming of multi-site stimulation, such as automated determination of the first and second stimulation vectors or the therapy mode including one or both of the chronological order and timing offset between the first and second stimulations delivered according to respective first and second stimulation vectors.

The method 600 may include a step 660 of delivering electrostimulation according to the selected vectors (such as LVa and LVb) and the therapy mode, including one or more of the chronological order or the timing offset. The first and second LV stimulations may be delivered during the same cardiac cycle, simultaneously or sequentially in the chronological order and the timing offset less than a sensed or paced interval value of a cardiac cycle, such as determined at 640 or adjusted or modified by the user at 652. In some examples, at 660 other therapies may be initiated or adjusted, including electrostimulation at non-cardiac tissues such as nerve tissues, or other types of therapies such as drug therapies, which may be used to restore cardiac function or prevent or slowdown the worsening of an existing cardiac disease such as heart failure.

In some examples, the method 600 may include steps of determining, in addition to the LVa and LVb vectors, other LV stimulation vectors or stimulation vectors for use in electrostimulation of one or more other heart chambers, such as RA, RV, or LA. The additional stimulation vectors may be determined using one or more of the response characteristics. The therapy mode, as determined at 640, may additionally include one or more of a chronological order and timing offsets associated with stimulations according to the other stimulation vectors. Examples of programming therapy mode for additional stimulation vectors are discussed below, such as with reference to FIG. 8.

Figure 7:
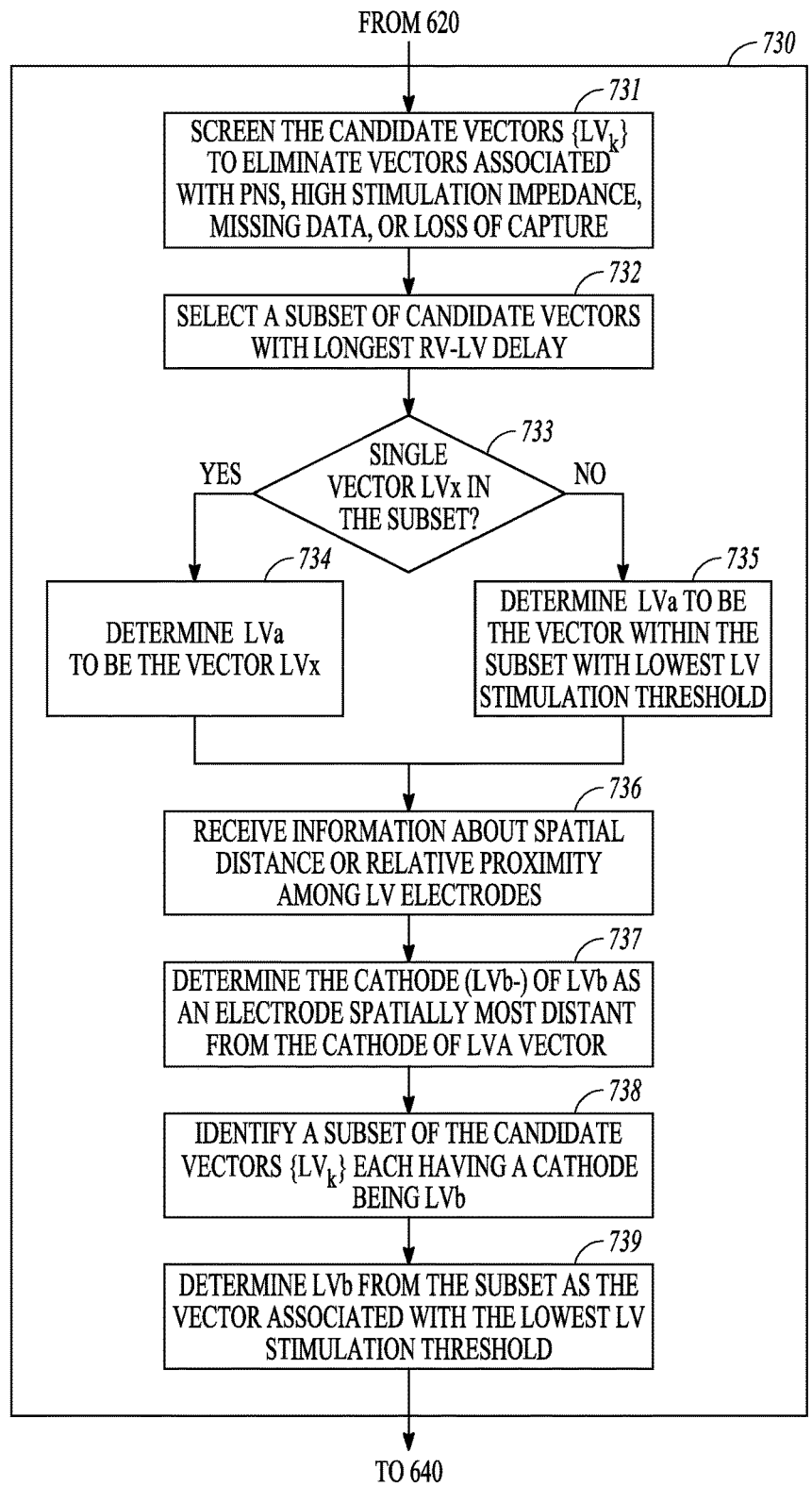
FIG. 7 illustrates generally an example of a method for determining first and second stimulation vectors for use in multi-site electrostimulation.

FIG. 7 illustrates generally an example of a method 730 for determining first (LVa) and second (LVb) stimulation vectors for use in multi-site electrostimulation. The method 730, which may be an embodiment of the step 650 of FIG. 6, may be implemented in and executed by the stimulation vector selector circuit 320, or any variant thereof.

At 731, the candidate vectors $\{LV_k\}$ are screened using criteria based on one or more response characteristics, such as stimulation efficacy indicators, complication indicators, or battery longevity indicators. A first set of candidate LV stimulation vectors that pass the screening process may be identified. The screening of the candidate vectors may include elimination of the vectors leading to PNS during stimulation, such as vectors associated with low PNS threshold ($PNS_T$) or a low safety margin (between LV stimulation threshold and the $PNS_T$) (e.g., falling below respective thresholds). The screening may additionally include eliminating the stimulation vectors associated with stimulation impedance measurements outside a specified range, such as outside the range of approximately 200-3000 ohms. The screening may additionally include eliminating the stimulation vectors associated with missing data or substantial amount of loss of capture during LV threshold testing.

At 732, a second set of stimulation vectors may be selected from the first set of candidate LV stimulation vectors provided at 731. RV–LV delay may be measured as timing difference between activations at a LV site and a RV site in response to electrostimulation of the heart according to a stimulation vector. The second set may include the LV stimulation vectors associated with substantially longer RV-LV delay than other of the first set of candidate LV stimulation vectors. If at 733 only one LV stimulation vector is identified to be included in the second set, then that vector may be determined to be the vector LVa at 734. If more than one vector is associated with substantially identical RV–LV delay or having a difference of RV-LV delay within a specified margin, the second set then may include two or more stimulation vectors. Then, at 735, the LVa vector may be determined to be the stimulation vector that corresponds to a lowest LV stimulation threshold among the stimulation vectors in the second set.

The LVa vector identified at 734 or 735 may be used for determining a second LV stimulation vector LVb, which includes a second LV cathode and a second anode. At 736, information about the spatial distance or relative proximity among LV electrodes may be received such as from a memory 260 or provided by a user such as via the user interface 250. At 737, the cathodes of the candidate LV stimulation vectors $\{LV_k\}$ are compared to the cathode of the vector LVa (denoted by "LVa–") to determine respective spatial distance to LVa–. The second cathode of the vector LVb (denoted by "LVb–") may be determined to be an electrode spatially most distant from the cathode of LVa vector, LVa–. In some examples, information about priority of cathodes may be used in determining the LVb vector. The priority information may be pre-determined and retrievably stored in a memory circuit. The second cathode (LVb–) of the vector LVb may be determined according to a priority as provided in Table 1.

At 738, a third set of candidate LV stimulation vectors may be identified from the candidate LV stimulation vectors $\{LV_k\}$, where each vector in this subset has a cathode as the electrode LVb– as determined at 736. The vector LVb may then be determined from the third set using one or more of response characteristics generated by the signal analyzer circuit 310, such as one or more of the stimulation efficacy indicators, complication indicators, or battery longevity indicators. As illustrated at step 739, the LVb vector may be determined from the third set as the vector associated with the lowest LV stimulation threshold. The LVb may alternatively be determined as the vector associated with the lowest power or current consumption among the third set of candidate LV stimulation vectors. In an example, the current consumption may be estimated using the LV stimulation threshold ($V_T$), stimulation impedance (Z), and the pulse width (PW) of the stimulation pulse, such as computed as $PW*V_T/Z$. In some examples, information about priority of anodes may be used in determining the LVb vector. For example, if two or more LV stimulation vectors in the third set of LV stimulation vectors (each having the second LV cathode) have substantially identical LV stimulation threshold, the vector that includes an anode of a highest priority may be determined as LVb. In an example, a descending order of priority may be represented by $E_{RVx}>E_x>$Can housing, where $E_{RVx}$ denotes an electrode on the RV and $E_x$ denotes an electrode on the LV that is different than the selected cathode of the LVb vector. In another example, if a most distal LV electrode E1 is selected to be the cathode of the LVb vector, a descending order of priority of the anodes may be represented by $E_{RVx}>$E4$>$E3$>$E2$>$Can housing.

The information about the spatial distance or relative proximity among LV electrodes may be specific to a particular type of lead. One or more of the steps 736-739 may be modified for a particular type of lead. In an example, the electrodes on the LV lead or catheter include a distal LV electrode and two or more proximal LV electrodes on the lead, where the distal LV electrode has an inter-electrode distance substantially greater than inter-electrode distance among the two or more proximal LV electrodes. If the cathode of the vector LVa is determined as one of the proximal LV electrodes, then the cathode of the vector LVb may be determined to be the distal electrode. Among the set of stimulation vectors identified at 738, the vector associated with the lowest LV stimulation threshold may be determined as the vector LVb. If the cathode of the vector LVa is determined to be the distal LV electrode, then among the candidate LV stimulation vectors each having a cathode being one of the proximal LV electrodes, the vector associated with the lowest LV stimulation threshold may be determined as the vector LVb. In another example, the electrodes on the LV lead or catheter include a plurality of distal electrodes and a plurality of proximal electrodes, and the distal and proximal electrodes are substantially equally spaced along the lead. If the cathode of the vector LVa is determined as one of the proximal LV electrodes, then among the candidate LV stimulation vectors each having a cathode being one of the distal LV electrodes, the vector associated with the lowest LV stimulation threshold may be determined as the vector LVb. Conversely, if he cathode of the vector LVb is determined as one of the distal LV electrodes, then among the candidate LV stimulation vectors each having a cathode being one of the proximal LV electrodes, the vector associated with the lowest LV stimulation threshold may be determined as the vector LVb. In yet another example, if the cathode of the LVa vector is selected to be an electrode positioned towards a basal region of the heart, then the cathode of the LVb vector may be selected to be an electrode positioned towards an apical region of the heart. Conversely, if the cathode of the LVa vector is selected to be an electrode positioned towards an apical region of the heart, then the cathode of the LVb vector may be selected to be an electrode positioned towards a basal region of the heart.

The method 700 may include an optional step of determining a third stimulation vector for electrostimulation at a third cardiac site different from the first and second LV sites. In an example, the third cardiac site includes a right ventricular (RV) site, and the third stimulation vector is a RV stimulation vector RVx that includes a RV cathode and an anode. In an example, determination of the third stimulation vector may be triggered by a user selection, such as via the user interface 250, of a "BiV" multi-site electrostimulation of various LV and RV sites. The selected stimulation vectors, such as LVa and LVb, or additionally with RVx, may be used for programming multi-site electrostimulation.

Figure 8:
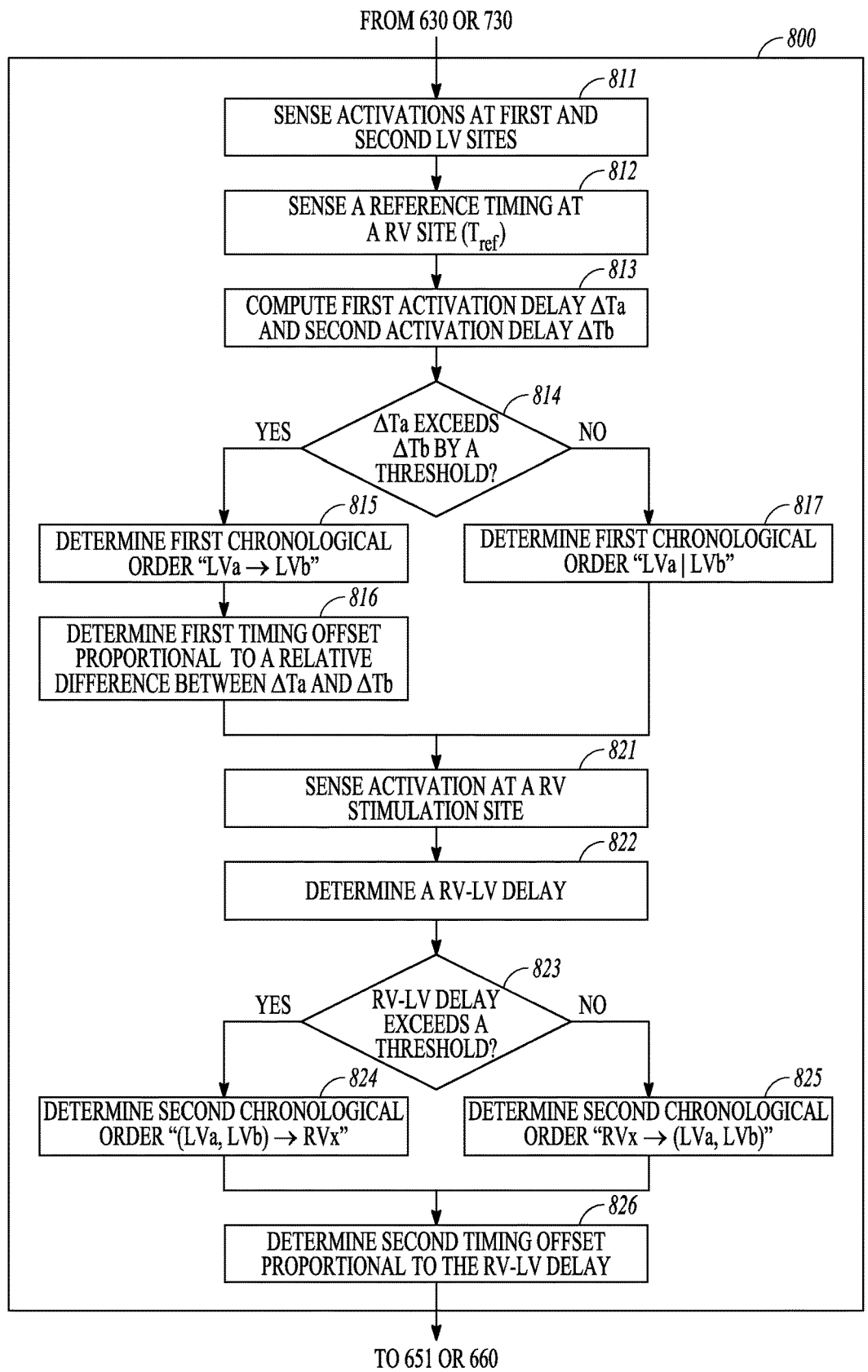
FIG. 8 illustrates generally an example of a method for programming a therapy mode for the selected stimulation vectors.

FIG. 8 illustrates generally an example of a method 800 for programming a therapy mode for the selected stimulation vectors. The therapy mode may include one or more of chronological orders, timing offsets, or stimulation parameters of stimulations respectively delivered according to selected stimulation vectors (such as determined at 630 in FIG. 6 or at 640 in FIG. 7. The method 800, which may be an embodiment of the step 640 of FIG. 6, may be implemented in and executed by the stimulation vector selector circuit 430, or any variant thereof.

The method 800 begins at 811 by sensing cardiac activations at the first and second LV sites, such as when the heart undergoes a specified intrinsic rhythm such as sinus rhythm or when the heart is stimulated according to a specified stimulation protocol such as RA pacing. The cardiac activation may include electrical activations such as sensed from an ECG or EGM, or mechanical activations such as sensed using an implantable or wearable sensor for sensing mechanical activity of the heart. At 812, a reference timing may be sensed, such as timing of an activation on a RV site. The RV activation may be sensed within the same cardiac cycle as the activations at the first and second LV sites. At 813, a first activation delay ($\Delta Ta$) between the activation at the first LV site and the RV activation and a second activation delay ($\Delta Tb$) between the activation at the second LV site and the RV activation may be computed. The first activation delay may be compared to the second activation delay at 814. If $\Delta Ta$ exceeds $\Delta Tb$ by a threshold, then the first chronological order may be determined at 815 to be "LVa→LVb", that is, the first LV stimulation according to the first stimulation vector LVa may precede the second LV stimulation according to the second stimulation vector LVb. If the criterion at 814 is not satisfied, then the first chronological order may be determined at 817 to be "LVa |LVb", that is, the first LV stimulation according to the LVa vector may be delivered substantially simultaneously with the second LV stimulation according to LVb vector. Corresponding to the chronological order "LVa→LVb", a first timing offset may be determined at 816 to be proportional to a difference between $\Delta Ta$ and $\Delta Tb$.

When a multi-site biventricular stimulation of both LV sites and RV sites ("BiV") is selected such as by a system user via the user interface 250, the method 800 may proceed to determine one or more of a second chronological order or a second timing offset. At 821, electrical or mechanical activation at a RV site may be sensed. A RV–LV delay can then be computed at 822. The RV–LV delay may be measured as a time interval between the LV activation (such as at the first or second LV site) and the RV activation within the same cardiac cycle. At 823, the RV-LV delay may be compared to a threshold. In an example, the threshold may be approximately 20 milliseconds. If the RV–LV delay exceeds the threshold, then at 824 a second chronological order may be determined such that the first and second LV stimulations precedes the third cardiac stimulation such as according to the RVx vector, denoted by "(LVa, LVb)→RVx" where (LVa, LVb) may be one of the chronological orders of LVa→LVb, LVb→LVa, or LVa|LVb as previously discussed. However, if the RV–LV delay falls below the specified threshold, then at 825 a second chronological order may be determined such that the third cardiac stimulation such as according to the RVx vector may precede the first and second LV stimulations, denoted by "RVx→(LVa, LVb)". At 826, a second timing offset corresponding to the second chronological order may be determined to be proportional to the RV–LV delay. The chronological order or the timing offset may also be edited by a system user via the user interface 250. The selected stimulation vectors and the therapy mode, such as the first and second chronological orders and the timing offsets, may be provided to a user or a process at 651 or 660.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. A system, comprising:
   an electrostimulation circuit configured to deliver electrostimulation to one or more sites in at least one chamber of a heart;
   a sensor circuit including a sense amplifier to sense a physiological signal including during the electrostimulation of the one or more candidate sites;
   a therapy programmer circuit in communication with the sensor circuit, the therapy programmer circuit configured to:
   determine, using the sensed physiological signal, a first stimulation vector for electrostimulation at a first left ventricular (LV) site, the first stimulation vector including a first LV cathode and a first anode;
   determine, based on the first stimulation vector, a second stimulation vector for electrostimulation at a different second LV site, the second stimulation vector including a second LV cathode and a second anode; and
   determine a therapy mode including one or more of a first chronological order or a first timing offset between (1) a first LV stimulation delivered according to the first stimulation vector and (2) a second LV stimulation delivered according to the second stimulation vector;
   a controller circuit to configure the electrostimulation circuit to deliver the first and second LV stimulations according to the therapy mode.

2. The system of claim 1, wherein:
   the sensor circuit is configured to detect, from the sensed physiological signal, activations at the first and second LV sites, and to determine a first activation delay from the activation at the first LV site with respect to a reference time, and a second activation delay from the activation at the second LV site with respect to the reference time; and
   the therapy programmer circuit is to determine the first chronological order or the first timing offset based on the first and second activation delays.

3. The system of claim 2, wherein the reference time includes a RV activation within the same cardiac cycle as the activations at the first and second LV sites, and
   wherein the therapy programmer circuit is to determine the first chronological order or the first timing offset including:
   the first LV stimulation substantially simultaneously delivered with the second LV stimulation, when the first activation delay is substantially no greater than the second activation delay; or
   the first LV stimulation preceding the second LV stimulation by the first timing offset proportional to a difference between the first activation delay and the second activation delay, when the first activation delay is substantially greater than the second activation delay.

4. The system of claim 1, wherein the therapy programmer circuit is further configured to:
   determine a third stimulation vector for electrostimulation at a third cardiac site different from the first and second LV sites; and
   determine a therapy mode further including one or more of a second chronological order or a second timing offset between (1) a third cardiac stimulation delivered according to the third stimulation vector and (2) the first or second LV stimulation.

5. The system of claim 4, wherein the third stimulation vector includes a RV cathode and an anode, and wherein:
   the sensor circuit is configured to detect from the sensed physiological signal a LV activation and a RV activation within the same cardiac cycle, and to determine a RV-LV delay from the detected LV activation to the detected RV activation; and
   the therapy programmer circuit is to determine the second chronological order or the second timing offset based at least on the RV–LV delay, including:
   the first and second LV stimulations preceding the third cardiac stimulation by a programmable offset when the RV–LV delay exceeds a specified threshold; and
   the third cardiac stimulation preceding the first and second LV stimulations by a programmable offset when the RV–LV delay falls below the specified threshold.

6. The system of claim 1, wherein:
   the electrostimulation circuit is configured to deliver electrostimulation according to each of a plurality of candidate LV stimulation vectors, each candidate LV stimulation vector including a LV cathode and an anode selected from the group consisting of a can electrode, a RV electrode, a right atrium electrode, a superior vena cava electrode and a different LV electrode;
   the sensor circuit is configured to generate, from the physiological signal sensed during the electrostimulation, one or more response characteristics associated with respective candidate LV stimulation vector; and
   the therapy programmer circuit is configured to determine the first stimulation vector including identify from the plurality of candidate LV stimulation vectors a LV stimulation vector with the corresponding one or more response characteristics satisfying a specified condition.

7. The system of claim 6, wherein the one or more response characteristics include:
   an indication of phrenic nerve stimulation (PNS);
   an impedance measurement;
   a RV to LV activation delay (VVD); or
   a LV stimulation threshold.

8. The system of claim 7, wherein the therapy programmer circuit is configured to select from the plurality of candidate LV stimulation vectors the first stimulation vector including:
   identify a first set of candidate LV stimulation vectors with substantially no PNS indication and the corresponding impedance measurements falling within a specified range;
   select from the first set of candidate LV stimulation vectors a second set of candidate LV stimulation vectors each having substantially longer VVD than other of the first set of candidate LV stimulation vectors; and if the second set of candidate LV stimulation vectors includes only one vector then determine the only one vector to be the first stimulation vector, or if the second set of candidate LV stimulation vectors includes more than one vectors then select from the second set the first stimulation vector having a substantially smaller LV stimulation threshold than other of the second set of candidate LV stimulation vectors.

9. The system of claim 7, wherein the therapy programmer circuit is configured to determine the second stimulation vector, including:

identify the second LV cathode selected from cathodes of the plurality of candidate LV stimulation vectors, the second LV cathode spatially more distant from the first cathode than other of the cathodes of the plurality of candidate LV stimulation vectors; and select, from a third set of candidate LV stimulation vectors each having the second LV cathode, the second stimulation vector associated with a substantially smaller LV stimulation threshold than other of the third set of candidate LV stimulation vectors.

10. The system of claim 1, wherein the therapy programmer circuit is configured to determine the second stimulation vector using information about relative inter-electrode distance among electrodes on a lead.

11. The system of claim 10, wherein the lead includes a distal LV electrode and two or more proximal LV electrodes, the distal LV electrode having an inter-electrode distance substantially greater than inter-electrode distance among the two or more proximal LV electrodes, and the therapy programmer circuit is configured to:

if the first LV cathode is determined as one of the proximal LV electrodes, then determine the second LV cathode as the distal electrode, and select from a set of candidate LV stimulation vectors each having a cathode being the distal LV electrode the second stimulation vector that has a substantially smaller LV stimulation threshold than other of the set of candidate LV stimulation vectors; or if the first LV cathode is determined to be the distal LV electrode, then select, from a set of candidate LV stimulation vectors each having a cathode being one of the proximal LV electrodes, the second stimulation vector that has a substantially smaller LV stimulation threshold than other of the set of candidate LV stimulation vectors.

12. The system of claim 1, wherein the therapy programmer circuit is configured to determine the therapy mode including determine one or more stimulation parameters for the first and second LV stimulation based on one or more of LV stimulation threshold at the first and second LV sites or complication indicators.

13. A system, comprising:

an ambulatory medical device, including:

an electrostimulation circuit configured to deliver electrostimulation to one or more sites in at least one chamber of a heart; and a sensor circuit including a sense amplifier to sense a physiological signal including during the electrostimulation of the one or more candidate sites; and a programmer device in communication with the ambulatory medical device, the programmer device including:

a therapy programmer circuit in communication with the sensor circuit, and configured to:

determine, using the sensed physiological signal, a first stimulation vector for electrostimulation at a first left ventricular (LV) site, the first stimulation vector including a first LV cathode and a first anode;

determine, based on the first stimulation vector, a second stimulation vector for electrostimulation at a different second LV site, the second stimulation vector including a second LV cathode and a second anode; and determine a therapy mode including one or more of a first chronological order or a first timing offset between (1) a first LV stimulation delivered according to the first stimulation vector and (2) a second LV stimulation delivered according to the second stimulation vector; and a user input unit coupled to the therapy programmer circuit, and configured to receive user instructions including the first and second LV stimulation vectors and the therapy mode.

14. A method for automatically programming multi-site electrostimulation via an electrostimulation system, the method comprising:

delivering electrostimulation to one or more sites in at least one chamber of a heart according to a plurality of candidate electrostimulation vectors;

sensing a physiologic signal including during the delivery of the electrostimulation;

determining, using the sensed physiological signal, a first stimulation vector for electrostimulation at a first left ventricular (LV) site, the first stimulation vector including a first LV cathode and a first anode;

determining, based on the first stimulation vector, a second stimulation vector for electrostimulation at a different second LV site, the second stimulation vector including a second LV cathode and a second anode; and determining a therapy mode for multi-site electrostimulation of at least the first and second LV sites, the therapy mode including one or more of a first chronological order or a first timing offset between (1) a first LV stimulation delivered according to the first stimulation vector and (2) a second LV stimulation delivered according to the second stimulation vector.

15. The method of claim 14, further comprising sensing from the sensed physiological signal activations at the first and second LV sites, and detecting a first activation delay from the activation at the first LV site with respect to a reference time, and a second activation delay from the activation at the second LV site with respect to the reference time; and wherein the first chronological order or the first timing offset is determined based on the first and second activation delays.

16. The method of claim 14, further comprising:

determining a third stimulation vector for electrostimulation at a third cardiac site at a right ventricle (RV), the third stimulation vector including a RV cathode and an anode;

detecting from the sensed physiological signal a LV activation and a RV activation within the same cardiac cycle; and determining a RV–LV delay from the detected LV activation to the detected RV activation; and wherein determining the therapy mode further includes determining one or more of a second chronological order or a second timing offset between (1) a third cardiac stimulation delivered according to the third stimulation vector and (2) the first or second LV stimulation based at least on the RV–LV delay.

17. The method of claim 14, wherein determining the first stimulation vector includes:
delivering electrostimulation according to each of a plurality of candidate LV stimulation vectors, each candidate LV stimulation vector including a LV cathode and an anode selected from the group consisting of a can electrode, a RV electrode, a right atrium electrode, a superior vena cava electrode and a different LV electrode;
generating, from the physiological signal sensed during the electrostimulation, one or more response characteristics associated with respective candidate LV stimulation vector; and
identifying from the plurality of candidate LV stimulation vectors a LV stimulation vector with the corresponding one or more response characteristics satisfying a specified condition,
wherein the one or more response characteristics including an indication of phrenic nerve stimulation (PNS), an impedance measurement, a RV to LV activation delay (VVD), or a LV stimulation threshold.

18. The method of claim 14, wherein determining the second stimulation vector includes:
identifying, from cathodes of the plurality of candidate LV stimulation vectors, the second LV cathode that is spatially more distant from the first cathode than other of the cathodes of the plurality of candidate LV stimulation vectors; and
selecting, from a third set of candidate LV stimulation vectors each having the second LV cathode, the second stimulation vector associated with a substantially smaller LV stimulation threshold than other of the third set of candidate LV stimulation vectors.

19. The method of claim 14, wherein the second stimulation vector is determined further using information about relative inter-electrode distance among electrodes on a lead.

20. The method of claim 14, wherein the determination of the therapy mode further includes determining one or more stimulation parameters for the first and second LV stimulation based on one or more of LV stimulation threshold at the first and second LV sites or complication indicators.

* * * * *